US008252292B2

(12) United States Patent
Fitz-Coy et al.

(10) Patent No.: US 8,252,292 B2
(45) Date of Patent: Aug. 28, 2012

(54) *EIMERIA* VACCINE FOR TURKEYS

(75) Inventors: Steve Hewart Fitz-Coy, Salisbury, MD (US); Gamini Saman Kumara Withanage, High Wycombe (GB); Alexandria Louise McGowan, High Wycombe (GB); Stephanie M. Cook, Omaha, NE (US)

(73) Assignees: Intervet International B.V., Boxmeer (NL); Intervet Inc., Summit, NJ (US)

( * ) Notice: Subject to any disclaimer, the term of this patent is extended or adjusted under 35 U.S.C. 154(b) by 220 days.

(21) Appl. No.: 12/616,341

(22) Filed: Nov. 11, 2009

(65) Prior Publication Data

US 2010/0166803 A1 Jul. 1, 2010

Related U.S. Application Data

(60) Provisional application No. 61/114,208, filed on Nov. 13, 2008.

(51) Int. Cl.
*A61K 39/012* (2006.01)
*A61K 39/00* (2006.01)
*A61K 39/002* (2006.01)
*C12N 1/00* (2006.01)
*C12N 1/36* (2006.01)

(52) U.S. Cl. .................. 424/267.1; 424/265.1; 435/243; 435/245

(58) Field of Classification Search ........................ None
See application file for complete search history.

(56) References Cited

U.S. PATENT DOCUMENTS

| | | | |
|---|---|---|---|
| 4,301,148 A | 11/1981 | Shibata et al. |
| 4,438,097 A | 3/1984 | Shirley |
| 4,935,007 A | 6/1990 | Bafundo et al. |
| 5,006,341 A | 4/1991 | Davis et al. |
| 5,055,292 A | 10/1991 | McDonald et al. |
| 5,882,672 A | 3/1999 | Kojima et al. |
| 6,306,385 B1 | 10/2001 | Lee |
| 6,432,646 B1 | 8/2002 | Gasser et al. |
| 6,495,146 B1 | 12/2002 | Evans et al. |
| 6,500,438 B2 | 12/2002 | Evans et al. |
| 6,908,620 B2 | 6/2005 | McDougald et al. |
| 6,969,602 B1 | 11/2005 | Danforth et al. |
| 6,998,126 B2 | 2/2006 | Davelaar |
| 6,998,127 B2 | 2/2006 | McDougald et al. |
| 7,018,640 B2 | 3/2006 | Evans et al. |
| 7,166,290 B2 | 1/2007 | Hutchins et al. |
| 7,211,265 B2 | 5/2007 | Richards et al. |
| 7,247,309 B2 | 7/2007 | Vermeulen et al. |
| 7,250,286 B2 | 7/2007 | Ellison |
| 7,354,593 B2 | 4/2008 | McDougald et al. |
| 2001/0005910 A1 | 6/2001 | Vermeulen et al. |
| 2002/0009765 A1 | 1/2002 | Lee et al. |
| 2002/0160022 A1 | 10/2002 | Schasteen et al. |
| 2004/0120973 A1 | 6/2004 | McDougald et al. |
| 2004/0175391 A1 | 9/2004 | Schasteen et al. |
| 2005/0244437 A1 | 11/2005 | Van Poppel et al. |
| 2006/0165731 A1 | 7/2006 | McDonald et al. |
| 2007/0026023 A1 | 2/2007 | McDougald et al. |
| 2008/0031896 A1 | 2/2008 | Vermeulen et al. |
| 2008/0131463 A1 | 6/2008 | Stewart-Brown et al. |
| 2010/0015182 A1 | 1/2010 | Lang et al. |

FOREIGN PATENT DOCUMENTS

| | | |
|---|---|---|
| EP | 0047662 | 3/1982 |
| EP | 0134703 | 3/1985 |
| EP | 0256878 | 2/1988 |
| EP | 0258045 | 3/1988 |
| EP | 0294941 | 12/1988 |
| EP | 0506211 | 9/1992 |
| EP | 0761103 | 3/1997 |
| EP | 0831896 | 4/1998 |
| EP | 0831897 | 4/1998 |
| EP | 1476558 | 11/2004 |
| EP | 1569687 | 9/2005 |
| WO | WO 85/00752 | 2/1985 |
| WO | WO 88/08699 | 11/1988 |
| WO | WO 95/34218 | 12/1995 |
| WO | WO 96/40233 | 12/1996 |
| WO | WO 96/40234 | 12/1996 |
| WO | WO 99/08704 | 2/1999 |
| WO | WO 99/50387 | 10/1999 |
| WO | WO 99/66953 | 12/1999 |
| WO | WO 01/68909 | 9/2001 |
| WO | WO 02/37961 | 5/2002 |
| WO | WO 03/020917 | 3/2003 |
| WO | WO 03/072044 | 9/2003 |
| WO | WO 2004/026903 | 4/2004 |
| WO | WO 2004/052393 | 6/2004 |
| WO | WO 2005/089262 | 9/2005 |
| WO | WO 2005/099617 | * 10/2005 |
| WO | WO 2006/113594 | 10/2006 |
| WO | WO 2009/148895 | 12/2009 |

OTHER PUBLICATIONS

Shirley, et al., "The Biology of Avian *Eimeria* with an Emphasis on their Control by Vaccination", Advances in Parasitology, vol. 60, pp. 285-330 (2005).
Thompson et al, "Clustal W: Improving the Sensitivity of Progressive Multiple Sequence Alignment Through Sequence Weighting, Position-Specific Gap Penalties and Weight Matrix Choice", Nucleic Acid Research, vol. 22, pp. 4673-4680 (1994).
Vermeulen, "Progress in Recombinant Vaccine Dexielopment Against Coccidiosis: A Review and Prospects into the Next Millennium", International Journal for Parasitology, vol. 28, pp. 1121-1130 (1998).
Williams, "Epidemiological Aspects of the Use of Live Anticoccidial Vaccines for Chickens", International Journal for Parasitology, vol. 28, No. 7, pp. 1089-1098 (1998).
Woods et al, "High-Resolution Electrophoretic Procedures for the Identification of Five *Eimeria* Species from Chickens, and Detection of Population Variation", Electrophoresis, vol. 21, pp. 3558-3563 (2000).
International Search Report for corresponding PCT/US2009/063977, mailed May 18, 2010.
Chapman, H.D. "Coccidlosis in the Turkey", Avian Pathology (Jun. 2008) 37(3):205-233.
Immucox Coccidiosis Vaccine for Turkeys, Product Information Sheet, Vetech Laboratories Inc. (www.vetechinc.com; Immucox@vetechinc.com).

* cited by examiner

*Primary Examiner* — Oluwatosin Ogunbiyi

(57) ABSTRACT

The present invention discloses a vaccine that provides protection to turkeys from coccidiosis, and methods of making and using the vaccine alone, or in combinations with other protective agents. In addition, the present invention discloses PCR primer sets that are useful in identifying the species of *Eimeria* in a biological sample.

18 Claims, 3 Drawing Sheets

Figure 1: Typical gross lesion seen with *E. meleagrimitis 2* in the duodenum.
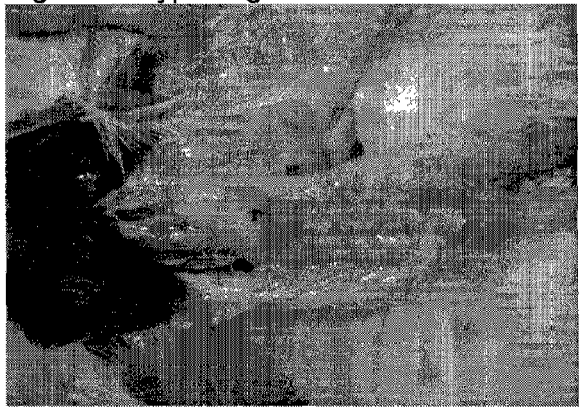
Figure 2: Typical gross lesion seen with *E. meleagrimitis 2* in the jejunum
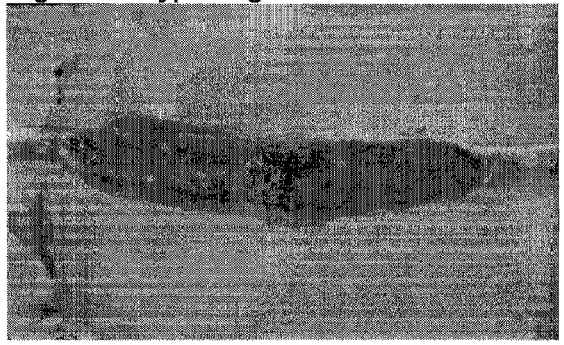
The feces of infected animals are watery, mucoid and bloody. The parasites invade the epithelial cells from the duodenum to the rectum and occasionally found in the ceca.

EIMERIA VACCINE FOR TURKEYS

CROSS-REFERENCE TO RELATED APPLICATIONS

This application claims priority under 35 U.S.C. §119(e) of provisional application U.S. Ser. No. 61/114,208 filed Nov. 13, 2008.

FIELD OF THE INVENTION

The present invention relates to a vaccine for turkeys that provides protection from coccidiosis. Methods of making and using the vaccine alone or in combinations with other protective agents are also provided. In addition, the present invention provides PCR primer sets that are useful in identifying pathogenic species of turkey *Eimeria*.

BACKGROUND

Coccidiosis is an enteric disease of animals that afflicts domestic poultry and livestock worldwide. Businesses that rely on animal production often face significant costs because of coccidiosis, including financial losses due to the diseased livestock, as well as the expenses for the prophylactic treatments intended to reduce and/or prevent the disease. Such costs are especially relevant to the commercial and intensive animal industries, such as the poultry industry, where intensive housing of birds favors the spread of coccidiosis.

Members of the obligate intracellular sporozoa subclass, Coccidia, are the etiological cause of coccidiosis. One genus of Coccidia, *Eimeria*, has a significant impact on animal production. As is true for closely related genera *Isospora, Cyclospora (Cystoisospora)*, and *Cryptosporidium, Eimeria* requires only a single host to complete its life cycle. Under natural conditions, this life cycle begins with the ingestion of sporulated oocysts from the environment.

*Eimeria* are single-celled parasites with a complex, monoxenous life cycle, that exhibit a high degree of both host-species and tissue specificity. *Eimeria* species include those that are found in chickens: *E. tenella, E. acervulina, E. maxima, E. necatrix, E. mitis, E. praecox, E. mivati, E. hagani* and *E. brunetti*; and those found in turkeys: *E. meleagrimitis* 1 (heretofore known simply as *E. meleagrimitis*), *E. adenoeides, E. gallopavonis, E. dispersa, E. meleagridis, E. innocua*, and *E. subrotunda*.

In the field of avian coccidiosis, the amount of research on turkey coccidia is dwarfed by the amount performed on chickens. Indeed, worldwide whereas there are only two commercially available turkey coccidia vaccines (Coccivac-T®, first used in 1960's and Immucox®, first used in the 1980's), there are approximately a dozen chicken coccidia vaccines. Therefore, there remains a particularly strong need for additional and improved vaccines that can provide protection for turkeys against avian coccidiosis.

Numerous *Eimeria* species can infect a single host via the oral route, nasal route and/or by entry of the infectious particles into the lacrimal duct. Once ingested, the parasites penetrate the intestinal mucosal cells and undergo asexual and sexual stages of the life cycle. The resulting intestinal damage can ultimately lead to impaired growth (stunting), decreased feed utilization, loss of pigmentation, and increased mortality. In addition, the damage to the intestinal lining can predispose turkeys to other infectious agents.

The stages of the life cycle of *Eimeria* are essentially the same for all species of *Eimeria*, although each species has a preferred site in the intestine for development and the time required to complete the life cycle varies from species to species. Infection begins with ingestion by a host of sporulated *Eimeria* oocysts. The ingested oocysts then release sporocysts in the intestine of the host. The sporocysts release sporozoites that enter intestinal epithelial cells and then transform into trophozoites. The trophozoites, in turn, undergo a process known as merogony to form first generation schizonts. Due to the relatively large schizonts, such as in the case of *E. necatrix* or *E. tenella*, or the abundance of the schizonts, such as *E. mivati*, or the large gamonts as in the case of *E. maxima*, these are the stages that cause the principal pathogenic effect of the infection, i.e., the tissue damage to the host.

Mature first generation schizonts produce numerous merozoites which are released and invade new epithelial cells, then grow and form the next-generation of schizonts. These asexual phases continue for a variable number of generations prior to the beginning of the sexual phase. The sexual phase starts when the schizonts develop into gamonts; microgamonts and macrogamonts. The microgamonts subsequently develop into microgametes that fertilize the macrogamonts to produce unsporulated oocyst progeny. The unsporulated oocysts are then released into the intestinal lumen and excreted with the host feces. The completion of the endogenous life cycle, heralded by emergence of unsporulated oocysts in the host feces, is known as patency.

Sporulation of the oocysts occurs outside of the host, when the environmental conditions are favorable. The inevitable ingestion by a host of the sporulated oocysts begins the next cycle of infection. The time from host ingestion of the sporulated oocysts to emergence of the unsporulated oocysts in the feces is termed the prepatent period. The prepatent period differs among the various *Eimeria* species.

Poultry that are repeatedly exposed to *Eimeria* infections can acquire immunity to coccidiosis. In fact, depending on the immunogenicity of each *Eimeria* species, daily infection of turkeys with small numbers of sporulated oocysts can result in the birds acquiring full immunity after as little as two repeated infections. Consequently, current protocols employing live *Eimeria* vaccines are based on the principle of acquired immunity, i.e., repeated infections with a small number of infective oocysts.

Vaccination generally is performed in the hatchery on the day of the bird's hatch by administering the live *Eimeria* vaccine via a spray application (directly onto the birds). Ingestion of the sporulated oocysts during normal preening of the feathers then results in an oral inoculation of the vaccine. Alternatively or in conjunction, vaccines can be applied at a later date in the feed and/or drinking water. The infective oocysts complete their life cycle inside the intestinal tract of the bird, as described above, culminating with the release of a new generation of unsporulated oocysts in 5-11 days, depending on the species of the *Eimeria*. The unsporulated oocysts excreted with the feces then become infective, i.e., sporulate outside of the host, and re-infect the birds through host ingestion. Following two or three such cycles, the birds become immunized against the species of coccidia that they previously were exposed to. This immunity is characterized by protection against the disease or infectious agents as determined by: (i) a decrease and/or absence of parasites observed microscopically in the intestine, (ii) a reduction of the shedding of the oocysts, (iii) a reduction of the intestinal lesions, (iv) a reduction of the clinical disease, (v) a reduction or prevention of weight lost, and/or (vi) a reduction in the impairment of the efficiency of feed utilization. The acquired immunity wanes over time in the absence of subsequent exposure to infective oocysts.

Wild-type *Eimeria* are generally isolated from outbreaks of clinical disease in poultry flocks and may be propagated for use as pathogenic challenge strains. Typical non-attenuated vaccines are composed of infective oocysts from mildly to moderately pathogenic strains of the different *Eimeria* species that have been maintained by laboratory passage. These non-attenuated *Eimeria* are capable of causing coccidiosis when ingested in very high numbers. Vaccine makers and users have to be careful to ensure that the vaccination provides just enough infective oocysts to elicit immunity, but not disease in the naïve host. After the initial dose, the vaccination process relies solely on re-infection through the host's ingestion of sporulated oocysts from the litter.

The pathogenicity, pathology, and clinical signs for coccidiosis in the turkeys may be characteristic for each *Eimeria* species. The *Eimeria* generally isolated from commercial turkey farms are *E. adenoeides, E. meleagrimitis* 1, *E. dispersa*, and *E. gallopavonis*; the four coccidia that heretofore, were considered to be the only pathogenic turkey *Eimeria* species. *E. adenoeides* and *E. gallopavonis* parasitize primarily the ceca and rectum, and in most cases the lower portion of the ileum. In contrast, *E. dispersa* and *E. meleagrimitis* 1 parasitize the small intestine with the parasitism mainly residing in the upper and mid-small intestine. Patho-physiological changes such as increased water loss via the feces, increased mucus production and/or blood loss due vascular damage, result in impaired performance such as reduced growth rate, feed utilization and even mortality.

Recent outbreaks of coccidiosis in commercial turkey flocks demonstrate that existing control methods cannot alone impede *Eimeria* infections. Indeed, in view of the lack of good control from pharmaceuticals and or vaccines to counteract such *Eimeria* infections, there remains a longfelt need for new and/or improved vaccines that can better protect turkeys from this costly enteric disease.

The citation of any reference herein should not be construed as an admission that such reference is available as "prior art" to the instant application.

SUMMARY OF THE INVENTION

Accordingly, the present invention provides new immunogenic compositions that comprise one or more *Eimeria* species that can help protect turkeys from coccidiosis. In one aspect of the present invention a vaccine is provided that comprises *E. meleagrimitis* 2 (also referred to as *E. edgari*) and *E. meleagrimitis* 1. In a particular embodiment of this type, the vaccine further comprises one or more additional *Eimeria* species selected from the group consisting of *E. adenoeides, E. gallopavonis, E. dispersa, E. innocua*, and *E. subrotunda*. In one particular embodiment the additional *Eimeria* species is *E. adenoeides*. In another embodiment the additional *Eimeria* species is *E. gallopavonis*. In yet another embodiment the additional *Eimeria* species is *E. dispersa*. In still another embodiment the additional *Eimeria* species is *E. innocua*. In yet another embodiment the additional *Eimeria* species is *E. subrotunda*.

Vaccines are also provided that comprise any and all combinations of such *Eimeria* species. In addition, vaccines are provided that comprise two or more strains of two or more of such individual species. In one embodiment of this type, the vaccine comprises pairs of strains of multiple *Eimeria* species in which multiple pairs of strains of single *Eimeria* species possess asynchronous prepatent periods. In a particular embodiment of this type, all of the pairs of strains of single *Eimeria* species in the vaccine possess asynchronous prepatent periods.

In another aspect of the invention, methods of immunizing a turkey against coccidiosis are provided. In one such embodiment the method of immunizing a turkey against coccidiosis comprises administering to the turkey a vaccine against *E. meleagrimitis* 2 comprising an immunologically effective amount *E. meleagrimitis* 2. In another embodiment, the method further comprises administering to the turkey one or more additional vaccines against a species of *Eimeria* other than *E. meleagrimitis* 2. In a particular embodiment of this type, each additional vaccine comprises an immunologically effective amount of one or more *Eimeria* species selected from the group consisting of *E. meleagrimitis* 1, *E. adenoeides, E. gallopavonis, E. dispersa, E. meleagridis, E. innocua*, and *E. subrotunda*. The administration of the vaccine against *E. meleagrimitis* 2 and the administration of one or more additional vaccines against a species of *Eimeria* other than *E. meleagrimitis* 2 can be performed in any order, including simultaneously in a combined multivalent administration.

Thus, the present invention provides methods that comprise administering to a turkey an immunologically effective amount of one or more of the turkey *Eimeria* species in a vaccine of the present invention. In a particular embodiment, such a vaccine is administered by spray application to the turkey. In another embodiment, the vaccine is administered in the drinking water of the turkey. In yet another embodiment, the vaccine is administered in the turkey feed. In still another embodiment the vaccine is both administered in the turkey feed and the drinking water. In yet another embodiment the vaccine is administered by spray application to the turkey, in the turkey feed, and/or in the drinking water In addition, any of the vaccines of the present invention that comprise strains of *Eimeria* can also include one or more species and/or strains of an *Isospora*, a *Cyclospora* (*Cystoisospora*), and/or a *Cryptosporidium*. In a particular embodiment of this type, the strain(s) of the species of *Isospora*, a *Cyclospora* (*Cystoisospora*), and/or a *Cryptosporidium* may also possess an asynchronous prepatent period.

The present invention further provides methods of identifying an *Eimeria* isolate as an *E. meleagrimitis* 2. One such embodiment comprises comparing the nucleotide sequence of the ITS-1 region of the genome of the *Eimeria* isolate with the nucleotide sequence of the ITS-1 region within SEQ ID NO: 44. The *Eimeria* isolate is identified as an *E. meleagrimitis* 2 when the entire nucleotide sequence of the ITS-1 region of the genome of the *Eimeria* isolate exhibits greater then 87% homology with the entire nucleotide sequence of the ITS-1 region within SEQ ID NO: 44. In a particular embodiment of this method, the *Eimeria* isolate is identified as an *E. meleagrimitis* 2 when the entire nucleotide sequence of the ITS-1 region of the genome of the *Eimeria* isolate exhibits greater than 95% homology with the entire nucleotide sequence of the ITS-1 region within SEQ ID NO: 44. In another embodiment of this method, the *Eimeria* isolate is identified as an *E. meleagrimitis* 2 when the entire nucleotide sequence of the ITS-1 region of the genome of the *Eimeria* isolate exhibits 100% identity with the entire nucleotide sequence of the ITS-1 region within SEQ ID NO: 44.

In particular embodiments the entire nucleotide sequence of the ITS-1 region of SEQ ID NO: 44 contains between 394 and 409 nucleotides. In other such embodiments, the entire nucleotide sequence of the ITS-1 region of SEQ ID NO: 44 contains between 400 and 409 nucleotides. In yet other embodiments, the entire nucleotide sequence of the ITS-1 region of SEQ ID NO: 44 contains between 395 and 400 nucleotides. In still other embodiments, the entire nucleotide sequence of the ITS-1 region of SEQ ID NO: 44 contains between 394 and 398 nucleotides. In yet other embodiments, the entire nucleotide sequence of the ITS-1 region of SEQ ID NO: 44 contains between 405 and 409 nucleotides. In still other embodiments, the entire nucleotide sequence of the ITS-1 region of SEQ ID NO: 44 contains 409 nucleotides.

In related embodiments the methods comprise comparing the nucleic acid sequence of the ITS-1 region of the genome of an *Eimeria* isolate with those specifically identified herein. In one such embodiment, the method comprises comparing the nucleic acid sequence of the ITS-1 region of the genome of an *Eimeria* isolate with the nucleic acid sequence of the ITS-1 region within a nucleotide sequence of SEQ ID NO: 31, SEQ ID NO: 32, SEQ ID NO: 33, SEQ ID NO: 34, and/or SEQ ID NO: 43. The *Eimeria* isolate is identified as an *E. meleagrimitis* 2 when the entire nucleic acid sequence of the ITS-1 region of the genome of the *Eimeria* isolate exhibits greater then 87% homology with the entire nucleic acid sequence of the ITS-1 region within the nucleotide sequence or sequences that it is being compared to. In another such embodiment, the *Eimeria* isolate is identified as an *E. meleagrimitis* 2 when the entire nucleic acid sequence of the ITS-1 region of the genome of the *Eimeria* isolate exhibits greater then 95% homology with the entire nucleic acid sequence of the ITS-1 region that is within the nucleotide sequence or sequences that it is being compared to. In yet another embodiment of this method, the *Eimeria* isolate is identified as an *E. meleagrimitis* 2 when the entire nucleotide sequence of the ITS-1 region of the genome of the *Eimeria* isolate exhibits 100% identity with the entire nucleotide sequence of the ITS-1 region within the nucleotide sequence that it is being compared to. Nucleotide sequence alignments can be performed with Clustal W methodology as described below.

The present invention also provides nucleic acids that comprise respectively, the nucleotide sequence of SEQ ID NO: 13, or SEQ ID NO: 14, or SEQ ID NO: 15, or SEQ ID NO: 16, or SEQ ID NO: 17, or SEQ ID NO: 18, or SEQ ID NO: 19, or SEQ ID NO: 20, or SEQ ID NO: 21, or SEQ ID NO: 22, or SEQ ID NO: 23, or SEQ ID NO: 24, or SEQ ID NO: 25, or SEQ ID NO: 26, or SEQ ID NO: 27, or SEQ ID NO: 28, or SEQ ID NO: 29, or SEQ ID NO: 30, or SEQ ID NO: 31, or SEQ ID NO: 32, or SEQ ID NO: 33, or SEQ ID NO: 34, or SEQ ID NO: 35, or SEQ ID NO: 36, or SEQ ID NO: 37, or SEQ ID NO: 38, or SEQ ID NO: 39, or SEQ ID NO: 40, or SEQ ID NO: 41, or SEQ ID NO: 42, or SEQ ID NO: 43, or SEQ ID NO: 44. In a particular embodiment such a nucleic acid comprises no more than 800 basepairs. In another embodiment such a nucleic acid comprises no more than 600 basepairs. In still another embodiment such a nucleic acid comprises no more than 500 basepairs. In a related embodiment, the nucleic acid can further comprise a heterologous nucleotide sequence.

The present invention further provides nucleic acids that comprise respectively, the nucleotide sequence of SEQ ID NO: 51, or SEQ ID NO: 52, or SEQ ID NO: 53, or SEQ ID NO: 54, or SEQ ID NO: 55, or SEQ ID NO: 56, or SEQ ID NO: 57, or SEQ ID NO: 58, or SEQ ID NO: 59, or SEQ ID NO: 60, or SEQ ID NO: 61, or SEQ ID NO: 62, or SEQ ID NO: 63, or SEQ ID NO: 64, or SEQ ID NO: 65, or SEQ ID NO: 66, or SEQ ID NO: 67, or SEQ ID NO: 68, or SEQ ID NO: 69, or SEQ ID NO: 70, or SEQ ID NO: 71, or SEQ ID NO: 72, or SEQ ID NO: 73, or SEQ ID NO: 74, or SEQ ID NO: 75, or SEQ ID NO: 76, or SEQ ID NO: 77, or SEQ ID NO: 78, or SEQ ID NO: 79, or SEQ ID NO: 80, or SEQ ID NO: 81. In a particular embodiment such a nucleic acid comprises no more than 800 basepairs. In another embodiment such a nucleic acid comprises no more than 600 basepairs. In still another embodiment such a nucleic acid comprises no more than 500 basepairs. In a related embodiment, the nucleic acid can further comprise a heterologous nucleotide sequence.

The present invention also provides a nucleic acid that comprises the nucleotide sequence of SEQ ID NO: 3. In another embodiment, the nucleic acid comprises the nucleotide sequence of SEQ ID NO: 4. In still another embodiment, the nucleic acid comprises the nucleotide sequence of SEQ ID NO: 5. In yet another embodiment, the nucleic acid comprises the nucleotide sequence of SEQ ID NO: 6. In still another embodiment, the nucleic acid comprises the nucleotide sequence of SEQ ID NO: 7. In yet another embodiment, the nucleic acid comprises the nucleotide sequence of SEQ ID NO: 8. In still another embodiment, the nucleic acid comprises the nucleotide sequence of SEQ ID NO: 9. In yet another embodiment, the nucleic acid comprises the nucleotide sequence of SEQ ID NO: 10. In still another embodiment, the nucleic acid comprises the nucleotide sequence of SEQ ID NO: 11. In yet another embodiment, the nucleic acid comprises the nucleotide sequence of SEQ ID NO: 12. In still another embodiment, the nucleic acid comprises the nucleotide sequence of SEQ ID NO: 45. In yet another embodiment, the nucleic acid comprises the nucleotide sequence of SEQ ID NO: 46. In still another embodiment, the nucleic acid comprises the nucleotide sequence of SEQ ID NO: 47. In yet another embodiment, the nucleic acid comprises the nucleotide sequence of SEQ ID NO: 48. In still another embodiment, the nucleic acid comprises the nucleotide sequence of SEQ ID NO: 49. In yet another embodiment, the nucleic acid comprises the nucleotide sequence of SEQ ID NO: 50.

Such nucleic acids can be used inter alia, as hybridization probes, or alternatively, as primers in polymerase chain reaction (PCR) amplifications to produce PCR products that correspond to portions and/or all of the ITS-1 regions of the respective genomes of the pathogenic turkey *Eimeria* species *E. adenoeides, E. meleagrimitis* 1, *E. dispersa, E. gallopavonis* and *E. meleagridis* 2, also known herein as *E. edgari*. In a particular embodiment, one or more of the aforementioned nucleic acids comprise 50 nucleotides or fewer. In still another embodiment, one or more of the aforementioned nucleic acids comprise 30 nucleotides or fewer. In still another embodiment, one or more of the aforementioned nucleic acids comprise only the number of nucleotides explicitly included in the sequence identified by the sequence identification number.

Any of the nucleic acids of the present invention can also include a heterologous nucleotide sequence. In addition, the present invention further provides nucleic acids that consist of the nucleotide sequences that are complementary to any of the nucleic acids provided herein.

The present invention further provides PCR primer pairs for amplifying an ITS-1 region of the genome of a species of turkey *Eimeria*. In one such embodiment the PCR primer pair comprises a first primer comprising a nucleotide sequence of SEQ ID NO: 3 and a second primer comprising a nucleotide sequence of SEQ ID NO: 4. In another embodiment the PCR primer pair comprises a first primer comprising a nucleotide sequence of SEQ ID NO: 5 and a second primer comprising a nucleotide sequence of SEQ ID NO: 6. In yet another embodiment the PCR primer pair comprises a first primer comprising a nucleotide sequence of SEQ ID NO: 7 and a second primer comprising a nucleotide sequence of SEQ ID NO: 8. In still another embodiment the PCR primer pair comprises a first primer comprising a nucleotide sequence of SEQ ID NO: 9 and a second primer comprising a nucleotide sequence of SEQ ID NO: 10. In yet another embodiment the PCR primer pair comprises a first primer comprising a nucleotide sequence of SEQ ID NO: 11 and a second primer comprising a nucleotide sequence of SEQ ID NO: 12. In still another embodiment the PCR primer pair comprises a first primer comprising a nucleotide sequence of SEQ ID NO: 45 and a second primer comprising a nucleotide sequence of SEQ ID NO: 46. In yet another embodiment the PCR primer pair comprises a first primer comprising a nucleotide sequence of SEQ ID NO: 47 and a second primer comprising a nucleotide sequence of SEQ ID NO: 48. In still another embodiment the PCR primer pair comprises a first primer comprising a nucleotide sequence of SEQ ID NO: 49 and a second primer comprising a nucleotide sequence of SEQ ID NO: 50.

The present invention additionally provides PCR amplification kits that comprise one, two or more PCR primer pairs of the present invention. Such kits can include any such combinations/permutations. Thus alternative kits of the present invention can comprise one, two, three, four, five, or more such PCR primer pairs.

For example, in one such kit, the respective nucleotide sequences of the first and second primer of one pair comprise SEQ ID NO: 11 and SEQ ID NO: 12. In another kit, the respective nucleotide sequences of the first and second primer of one pair comprise SEQ ID NO: 3 and SEQ ID NO: 4, and the respective nucleotide sequences of the first and second primer of another pair comprise SEQ ID NO: 11 and SEQ ID NO: 12. In yet another kit, the respective nucleotide sequences of the first and second primer of one pair comprise SEQ ID NO: 5 and SEQ ID NO: 6, and the respective nucleotide sequences of the first and second primer of another pair comprise SEQ ID NO: 11 and SEQ ID NO: 12.

In still another such kit, the respective nucleotide sequences of the first and second primer of one pair comprise SEQ ID NO: 5 and SEQ ID NO: 6, the respective nucleotide sequences of the first and second primer of another pair comprise SEQ ID NO: 9 and SEQ ID NO: 10, and the respective nucleotide sequences of the first and second primer of yet an additional pair comprise SEQ ID NO: 11 and SEQ ID NO: 12.

In a particular embodiment, the kit comprises PCR primer pairs that respectively have primer pairs comprising the nucleotide sequence of SEQ ID NO: 3 and SEQ ID NO: 4, SEQ ID NO: 5 and SEQ ID NO: 6, SEQ ID NO: 7 and SEQ ID NO: 8, SEQ ID NO: 9 and SEQ ID NO: 10, and SEQ ID NO: 11 and SEQ ID NO: 12. Alternatively, in certain kits, SEQ ID NO: 45 and SEQ ID NO: 46 can be substituted for SEQ ID NO: 7 and SEQ ID NO: 8; and/or SEQ ID NO: 47 and SEQ ID NO: 48 substituted for SEQ ID NO. 5 and SEQ ID NO: 6; and/or SEQ ID NO. 49 and SEQ ID NO: 50 substituted for SEQ ID NO. 9 and SEQ ID NO: 10.

In still another embodiment, a kit of the present invention comprises PCR primer pairs that respectively have primer pairs comprising the nucleotide sequence of SEQ ID NO: 3 and SEQ ID NO: 4, SEQ ID NO: 5 and SEQ ID NO: 6, SEQ ID NO: 45 and SEQ ID NO: 46, SEQ ID NO: 47 and SEQ ID NO: 48, and SEQ ID NO: 49 and SEQ ID NO: 50.

The present invention further provides methods of employing one or more pairs of PCR primers to identify one or more pathogenic species of turkey *Eimeria* in a biological sample. One such method can be used to identify *E. meleagrimitis* 2 in a biological sample. A particular embodiment of this method comprises accessing nucleic acids contained by a biological sample and amplifying them by PCR in the presence of a PCR primer pair specific for *E. meleagrimitis* 2 under conditions that will produce a PCR product when nucleic acids from *E. meleagrimitis* 2 are contained by the biological sample. The production of the PCR product is monitored, and when the PCR product is detected, *E. meleagrimitis* 2 is identified as being in the biological sample. In a particular embodiment of this type, the respective nucleotide sequences of the first and second primer of the PCR primer pair employed comprises SEQ ID NO: 11 and SEQ ID NO: 12, respectively. In yet another embodiment, the PCR product(s) produced are sequenced and when they are found to have greater than 87% homology with the corresponding nucleotide sequence contained within SEQ ID NOs: 31, 32, 33, 34, 43, and/or 44, *E. meleagrimitis* 2 is identified as being present in the sample.

In still another embodiment, the PCR product(s) produced are sequenced and when they are found to have greater than 95% homology with the corresponding nucleotide sequence contained within SEQ ID NOs: 31, 32, 33, 34, 43, and/or 44, *E. meleagrimitis* 2 is identified as being present in the sample. In yet another embodiment, the PCR product(s) produced are sequenced and when they are found to have 100% identity with the corresponding nucleotide sequence contained within SEQ ID NOs: 31, 32, 33, 34, 43, and/or 44, *E. meleagrimitis* 2 is identified as being present in the sample.

In another embodiment, a method of identifying pathogenic turkey *Eimeria* present in a biological sample comprises accessing nucleic acids contained by the biological sample and amplifying the accessed nucleic acids by PCR in the presence of a complete set of primers for the now five known pathogenic turkey *Eimeria* species under conditions that will produce the corresponding PCR product(s) when the corresponding nucleic acids from the pathogenic turkey *Eimeria* are contained by the biological sample. The PCR product(s) are monitored, and when any of the PCR product(s) are detected during the monitoring, pathogenic turkey *Eimeria* are identified as being in the biological sample.

In a related embodiment, a method of identifying the species of pathogenic turkey *Eimeria* present in a biological sample comprises accessing nucleic acids contained by a biological sample and amplifying the accessed nucleic acids by PCR in the presence of a complete set of primers for the pathogenic turkey *Eimeria* species under conditions that will produce the corresponding PCR product(s) when the corresponding nucleic acids from the pathogenic turkey *Eimeria* are contained by the biological sample. The PCR product(s) are detected and the species of the pathogenic turkey *Eimeria* associated with each PCR product detected are determined. The determination can thus identify each species of pathogenic turkey *Eimeria* present in the biological sample.

In particular embodiments, the nucleotide sequence(s) of the PCR product(s) produced are determined. When such a nucleotide sequence has greater than 87% homology with the corresponding nucleotide sequence contained within SEQ ID NOs: 31, 32, 33, 34, 43, and/or 44, *E. meleagrimitis* 2 is identified as being present in the sample. Similarly, when the nucleotide sequence of a PCR product produced has greater than 90% homology with the corresponding nucleotide sequence contained within SEQ ID NOs: 24, 25, 26, 27, 28, 29, and/or 30, *E. meleagrimitis* 1 is identified as being present in the sample. When the nucleotide sequence of a PCR product produced has greater than 90% homology with the corresponding nucleotide sequence contained within SEQ ID NOs: 18, 19, 20, and/or 21, *E. adenoeides* is identified as being present in the sample. When the nucleotide sequence of a PCR product produced has greater than 90% homology with the corresponding nucleotide sequence contained within SEQ ID NOs: 13, 14, 15, 16, 17, 36, 39, 40, and/or 41, *E. gallopavonis* is identified as being present in the sample. Finally, when the nucleotide sequence of a PCR product produced has greater than 90% homology with the corresponding nucleotide sequence contained within SEQ ID NOs: 22, 23, and/or 42, *E. dispersa* is identified as being present in the sample. In related embodiments, the percent homology required can be set to greater than 95%, and even to 100% identity for selected species when desired.

In one particular embodiment the PCR primer pair specific for *E. meleagrimitis* 2 comprises the nucleotide sequences of SEQ ID NO: 11 and SEQ ID NO: 12, respectively; the PCR primer pair specific for *E. meleagrimitis* 1 comprises the nucleotide sequences of SEQ ID NO: 3 and SEQ ID NO: 4, respectively; the PCR primer pair specific for *E. adenoeides* comprises the nucleotide sequences of SEQ ID NO: 5 and SEQ ID NO: 6 respectively; the PCR primer pair specific for *E. gallopavonis* comprises the nucleotide sequences of SEQ ID NO: 7 and SEQ ID NO: 8, respectively; and the PCR primer pair specific for *E. dispersa* comprises the nucleotide sequences of SEQ ID NO: 9 and SEQ ID NO: 10, respectively.

In another related embodiment, a method of identifying the species of pathogenic turkey *Eimeria* present in a biological sample comprises isolating one or more turkey *Eimeria* isolates from the biological sample and ascertaining one or more properties of the pathogenic turkey *Eimeria* isolated. These properties include, but are not limited to the pathology, the pathogenicity, the cross-immunity, and/or the morphometrics of the turkey *Eimeria* isolate(s). In a particular embodiment of this type, the method further includes employing one or more genetic analyses (e.g., PCR) in conjunction with ascertaining one or more properties of the pathogenic turkey *Eimeria*. When more than one method of identifying the species of pathogenic turkey *Eimeria* present in a biological sample is performed, such methods can be run in any order, including simultaneously, if feasible.

These and other aspects of the present invention will be better appreciated by reference to the Detailed Description, Figures, and Examples.

BRIEF DESCRIPTION OF THE DRAWINGS

FIG. 1 shows typical gross lesions seen with *E. meleagrimitis* 1 or *E. meleagrimitis* 2 in the duodenum.

FIG. 2 shows typical gross lesions seen with *E. meleagrimitis* 1 or *E. meleagrimitis* 2 in the jejunum.

DETAILED DESCRIPTION OF THE INVENTION

Figure 3A:
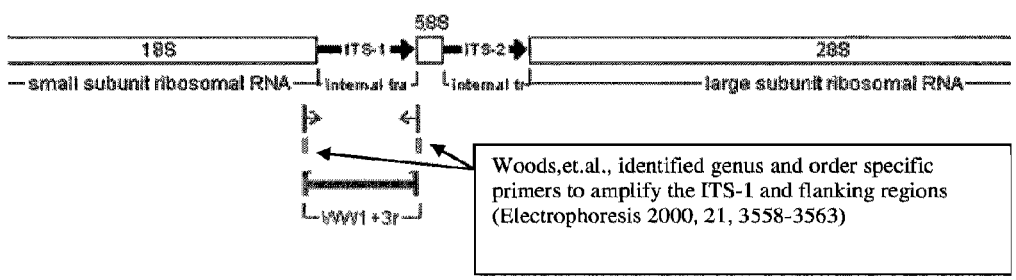
FIG. 3A shows the location of ITS-1 PCR primers.

In one aspect, the present invention provides a newly identified pathogenic species of *Eimeria*, which has been named *E. meleagrimitis* 2 (or alternatively, *E. edgari*). As further provided herein, *E. meleagrimitis* 2 has been sufficiently characterized to allow its unequivocal identification. In a related aspect, the present invention provides new vaccines that protect against this newly identified pathogenic species of *Eimeria*. In still another aspect, the present invention provides kits that can be used to readily identify and distinguish the now five known pathogenic species of turkey *Eimeria*.

*E. meleagrimitis* 2 was isolated from outbreaks of clinical coccidiosis in commercial turkey operations from several states throughout the US, and from wild turkeys living in the Delmarva region. *E. meleagrimitis* 2 (Eme2) affects the same region of the intestine as *E. meleagrimitis* 1, however Eme2 can be differentiated by morphology of oocysts, conferred immunity (cross-protection studies), and by DNA sequence.

Heretofore, there have been no vaccines that provided protection against both *E. meleagrimitis* 2 and *E. meleagrimitis* 1. Therefore, in one key aspect, the present invention provides vaccines that protect against both *E. meleagrimitis* 2 and *E. meleagrimitis* 1. In one such embodiment, the vaccine comprises both *E. meleagrimitis* 2 and *E. meleagrimitis* 1. In a related aspect, methods of administering the vaccines of the present invention are provided.

In addition, the present invention provides sequence analysis of the Internal Transcribed Spacer region one (ITS-1) located between the 18S and 5.8S ribosomal RNA genes in the *Eimeria* genome, for each of the pathogenic *Eimeria* species: *E. meleagrimitis* 1, *E. adenoeides*, *E. gallopavonis*, *E. dispersa*, and *E. meleagrimitis* 2. Therefore, in yet another key aspect, the present invention provides nucleic acids comprising nucleotide sequences that uniquely identity these five pathogenic *Eimeria* species.

The present invention further provides diagnostic kits and related methods that employ polymerase chain reaction (PCR) primer sets capable of identifying each of these five pathogenic *Eimeria* species. In a particular embodiment, such primers and/or primer sets and/or unique nucleotide sequences provided herein, can be used to distinguish *E. meleagrimits*, *E. adenoeides*, *E. gallopavonis*, *E. dispersa*, and/or *E. meleagrimitis* 2 from each other.

The use of singular terms for convenience in description is in no way intended to be so limiting. Thus, for example, reference to a composition comprising "a quantity" includes reference to one or more of such quantities. In addition, reference to an "oocyst" includes reference to a plurality of such oocysts, unless otherwise indicated.

All nucleic acid sequences provided herein, unless indicated to the contrary, are written 5' to 3'.

As used herein the following terms shall have the definitions set out below:

The term "turkey", as used herein, and unless otherwise indicated, includes all of the members of the genus *meleagris*, including the species *gallopavo* and *ocellata*. Almost all domestic turkeys belong to the species *gallopavo*.

The term "biological sample" as used herein is any sample obtained from an animal, e.g., turkey, or from the animal's surroundings (e.g., litter, and/or geographical area where animals reside and/or range) that contains and/or is suspected to contain *Eimeria*, and/or nucleic acids from and/or derived from *Eimeria*. Examples of biological samples include, but are not limited to: fecal samples, litter samples, and gastrointestinal samples.

As used herein the term "accessing nucleic acids" contained by a biological sample means ensuring that the nucleic acids of the biological sample are available to serve as a template during PCR. In the simplest case, accessing the nucleic acids entails placing a biological sample into the PCR reaction vessel. However, this term can also include one or more manipulations of a biological sample, e.g., cell fracturing/lysis, purification steps, etc., that aid in making the nucleic acids contained by the biological sample available to serve as a template during PCR.

The term "*Eimeria*", as used herein, unless otherwise indicated, means one or more species of the genus *Eimeria* that infect domesticated birds. *Eimeria* species include those that are found in chickens, and include, e.g., *E. tenella*, *E. acervulina*, *E. maxima*, *E. necatrix*, *E. mitis*, *E. praecox*, *E. mivati*, *E. hagani* and *E. brunetti*, and also those that are found in turkeys, including *E. meleagrimitis* 1, *E. adenoeides*, *E. gallopavonis*, *E. dispersa*, *E. meleagridis*, *E. innocua*, and *E. subrotunda*. As used herein, a "turkey *Eimeria*" refers to *Eimeria* that infect turkeys. The term "*Eimeria*" also includes all strains of the foregoing species of *Eimeria*, including, but not limited to, precocious strains, and attenuated strains, which also includes strains that have been irradiated, or otherwise treated, so that they fail to complete development. The term *Eimeria* further includes any newly-discovered strains or species of *Eimeria* that infect domesticated birds as defined above, such as *E. meleagrimitis* 2 as disclosed herein.

As used herein the term "E. MAD" signifies a mixture of *E. meleagrimitis* 1, *E. adenoeides*, and *E. dispersa*.

As used herein, an "attenuated" strain of a species of a Coccidia genus (such as an "attenuated *Eimeria*") is a strain that has been selected for its reduced pathogenicity in the host. Such attenuation can be achieved by a number of means including serial passage (such as serial embryo passage), chemical mutagenesis, or by irradiation methods.

As used herein, a "precocious" strain of a species of a Coccidia genus (such as a "precocious *Eimeria*") is a strain that has a shortened prepatent period relative to the non-attenuated strain of the same species. A precocious strain can also be an attenuated strain.

As used herein, a "wild-type" strain of a species of a Coccidia genus (such as a "wild-type *Eimeria*") is a field isolate which has not been altered by attenuating passage or any other treatment including selection by: single oocyst isolation, immune tolerance, or other segregative process.

As used herein, a "non-attenuated" strain of a species of a Coccidia genus (such as "non-attenuated *Eimeria*") is a strain that neither has a shortened prepatent period nor reduced pathogenicity in the host relative to the wild-type strain of the same species, but has been maintained in the laboratory for an extended time.

As used herein, a "strain" of a species of a Coccidia genus (e.g., a species of *Eimeria*) is a subpopulation of the species of the Coccidia genus that can be differentiated from the general population of that species by one or more of the following features: morphometrics, pathogenicity, immunogenicity, prepatent period, and/or a population resulting from expansion of a single oocyst.

As stated above, the time from host ingestion of the sporulated oocysts to emergence of the unsporulated oocysts in the feces is termed the prepatent period. The term "asynchronous prepatent period" refers to prepatent periods of two or more species of a Coccidia genus and/or two or more strains of a species of a Coccidia genus that differ by 10% or greater. In a particular embodiment, two or more species of a Coccidia genus and/or two or more strains of a single species of a Coccidia genus have asynchronous prepatent periods that differ by 20% or greater. In still another embodiment, two or more species of a Coccidia genus and/or two or more strains of a single species of a Coccidia genus have asynchronous prepatent periods that differ by 25% or greater.

In reference to asynchronous prepatent periods for precocious and/or attenuated strains with non-attenuated strains that differ by a percentage (%) of time, the percentage is based on the non-attenuated strain's prepatent time period. Thus, when a non-attenuated strain of a Coccidia genus has a prepatent period of 120 hours and a precocious strain of the same species of the Coccidia genus has a prepatent period of 108 hours, the two strains have asynchronous prepatent periods that differ by 10%.

As used herein, a "homologous material" is a composition and/or aliquot of: organisms that have uniform biological properties, and/or are derived from organisms of the same species, and/or show a degree of similarity of properties that indicates a common origin.

As used herein, a "heterologous material" is a composition and/or aliquot of: organisms that have different biological properties, and/or are derived from organisms of different species, and/or show a degree of dissimilarity of properties that indicates different origins.

The terms "oocysts", "merozoites" and "sporozoites", as used herein, and unless otherwise indicated, mean turkey *Eimeria* oocysts, merozoites, and sporozoites that can be either killed, attenuated, or non-attenuated.

The term "sporocyst" refers to the capsule that encloses the sporozoites in the oocyst.

The term "encysted" means the oocyst stage of the protozoan parasite.

As used herein, the terms "immunize" and "vaccinate" are synonymous and are used interchangeably. The term "effective immunizing dose", as used herein, unless otherwise indicated, means the number of sporozoans at any stage in their life-cycle including mixtures of one or more, or even all stages of their life-cycles, e.g., sporozoites, oocysts and/or merozoites, or, when mixed, e.g., the number of sporozoites, oocysts and merozoites, sufficient to elicit an immune reaction in animals so vaccinated, e.g., elicit a rise in corresponding antibody titers and/or an activation of cell-mediated immunity. Preferably, the immune reaction that is elicited provides protective immunity that limits or reduces clinical disease signs, weight loss, morbidity, decreased feed utilization, and/or mortality in the vaccinated animals (e.g., avians) when challenged with a virulent dose of the sporozoa (e.g., *Eimeria* or *Cryptosporidia*).

The term "solid immunity" is used interchangeably herein with the term "full immunity" and the term "hyper-immunity", and denotes a degree of immunity bestowed on a group of vaccinated animals (e.g., a flock of vaccinated birds) that provides protection against an homologous challenge such that the vaccinated animals are statistically similar to non-challenged controls (and/or statistically dissimilar to non-vaccinated challenged controls) in health and performance as measured by e.g., feed conversion, weight gain, and/or lesions (gross or microscopic) of coccidiosis.

The terms "adjuvant" and "immune stimulant" are used interchangeably herein, and are defined as one or more substances that cause stimulation of the immune system. Adjuvants are agents that nonspecifically increase an immune response to a particular antigen, thus reducing the quantity of antigen necessary in any given vaccine, and/or the frequency of injection necessary in order to generate an adequate immune response to the antigen of interest. In this context, an adjuvant is used to enhance an immune response to one or more vaccine antigens/isolates. An adjuvant may be administered to the target animal before, in combination with, or after the administration of the vaccine.

As used herein a "heterologous nucleotide sequence" is a nucleotide sequence that is added to a nucleotide sequence of the present invention by recombinant methods to form a nucleic acid that is not naturally formed in nature. Such nucleic acids can encode fusion (e.g., chimeric) nucleic acids. In a particular embodiment the heterologous nucleotide sequence can function as a means of detecting a nucleotide sequence of the present invention. In another embodiment such a heterologous nucleotide sequence can function to facilitate the use of the nucleic acid in a PCR reaction.

As used herein the term "approximately" is used interchangeably with the term "about" and signifies that a value is within fifty percent of the indicated value i.e., a composition containing "approximately" 100 oocysts contains from 50 to 150 oocysts.

The term "statistically similar" as used herein denotes that a statistical comparison of the two groups or populations of animals would result in acceptance of the null hypothesis (or hypothesis of no difference) at a level of significance of <0.1.

The term "statistically dissimilar" as used herein denotes that a statistical comparison of the two groups or populations of animals would result in rejection of the null hypothesis (or hypothesis of no difference) at a level of significance of <0.1.

As used herein, when a series of nucleotide sequences are provided by a list of SEQ ID NOs., e.g., SEQ ID NOs: 31, 32, 33, 34, and/or 43 (or SEQ ID NO:31, SEQ ID NO:32, SEQ ID NO:33, SEQ ID NO:34, and/or SEQ ID NO:43), the "and/or" is intended to modify the relationship between all of the SEQ ID NOs. listed in the series. Therefore, a comparison/identification based on such a series of nucleotide sequences can be made with reference to any one of the individual nucleotide sequences listed alone, or to any combination of the individual nucleotide sequences listed, including to all of the nucleotide sequences listed in the series.

Nucleotide sequence alignments are performed using Clustal W methodology based on J. D. Thompson et al., [Nucleic Acid Research 22:4673-4680 (1994)], in Megalign™ alignment program of DNASTAR data analysis software (Windows 32 Megalign 5.06. 1993-2203 DNASTAR Inc.) using default settings throughout.

Characterization of E. meleagrimitis 2

E. meleagrimitis 2 invades the same regions of the intestines as E. meleagrimitis 1 and E. dispersa, but the oocysts of E. meleagrimitis 2 are relatively smaller than those of these two species. The sporulated oocysts examined were found to be subspherical, measuring 17.824×16.444 microns (16.915-19.549×14.585-18.314 microns) with a shape index of 1.0839.

Parasitism with E. meleagrimitis 2 is accompanied by severe hyperemia and excessive mucus production in the upper half of the small intestine, with moderate to severe mucosal hemorrhage extending from the duodenum to the ileum as the infection progresses (see, FIGS. 1 and 2).

The newly identified Eimeria species E. meleagrimitis 2, can be unequivocally identified by its unique nucleotide sequence in the Internal Transcribed Spacer region one (ITS-1 region, see, FIG. 3B), located between the 18S and 5.8S ribosomal RNA genes in the Eimeria genome. Accordingly, the present invention provides individual nucleotide sequences of the ITS-1 region of four E. meleagrimitis 2 isolates, SEQ ID NOs: 31, 32, 33, and 39. These sequences share greater than 96% (and up to 100%) homology with each other. The present invention further provides a consensus sequence for the ITS-1 region of E. meleagrimitis 2 with a nucleotide sequence of SEQ ID NO: 44.

In addition, PCR primer sets, based on the ITS-1 region sequence of each species, have been designed for use in PCR-based identity assays. A complete set of such primers are contained within the group of pairs of nucleotide sequences of SEQ ID NOs: 3 and 4, for E. meleagrimitis 1; SEQ ID NOs: 5 and 6, for E. adenoeides; SEQ ID NOs: 7 and 8, for E. gallopavonis; SEQ ID NOs: 9 and 10, for E. dispersa; SEQ ID NOs: 11 and 12, for E. meleagrimitis 2.

Animal Subjects

The animal to be so treated is preferably a member of the genus Meleagris, i.e., a turkey. In a particular embodiment, the turkey is of the genus gallopavo, i.e., a domestic turkey. In another embodiment, the turkey is of the genus ocellata. Generally, the administration of the vaccine will be performed on young turkey poults, oftentimes, on the day of hatch of the turkey poult.

Antigens

Wild type oocysts are obtainable from feces or tissue of infected animals; contaminated feed or water; soil; pen litter or bedding; or a variety of other sources. Methods for isolation of sporocysts and oocysts are known. The exact procedures used to separate oocysts will vary with the material from which the oocysts are obtained and will be readily apparent to those skilled in the art. Merozoites can be grown in culture by the methods disclosed in U.S. Pat. No. 7,250,286 B2, the contents of which are hereby incorporated by reference in their entireties.

One available approach to isolating organisms from raw environmental samples is as follows: The initial step is separation of the sporocysts and/or oocysts from extraneous material. Soil or excreta is generally processed by forming a slurry with saturated saline solution and separating the sporocysts and/or oocysts from the slurry. For example, the material to be processed is mixed with a minimum of 2 volumes (w/v) of saturated aqueous NaCl to form a slurry. If necessary, the slurry can be processed in a mixer or blender until a homogenous consistency is achieved. The slurry is centrifuged at about 800×g for 10 minutes at 4° C. The supernatant is collected by pouring through a double layer of 24×24 weave cheese cloth. Other methods to purify oocysts from samples that are commonly used include the Sheather sucrose flotation and Zinc-sulfate flotation, [e.g., see L R Ash and T C Orihel, Parasites: A Guide to Laboratory Procedures and Identification, ASCP Press © 1991, incorporated by reference herein].

The filtered supernatant is diluted with two volumes of potable water and centrifuged at about 1600×g for 10 minutes at 4° C. The pelleted oocysts are washed with water and pelleted by centrifugation as described an additional three times. The oocysts are then washed three times in 2.5% potassium dichromate using the same procedure used for the water washes. After the final wash, the oocysts can be stored in 2.5% potassium dichromate at 4° C. or transferred to a container for sporulation.

Alternatively, sequential filtration can be used to isolate oocysts based on size. If filtration is used, the oocysts are washed with water and 2.5% potassium dichromate as previously described.

Non-attenuated lines that originated as wild-type field isolates have been maintained in laboratory settings by serial passage over many years and are well characterized as low to moderate in pathogenicity, with moderate to high fecundity, defined prepatent periods and known patterns of shedding from the host.

Aside from existing precocious Eimeria lines, precocious lines also can be obtained from wild-type, virulent parent strains or non-attenuated strains following serial passage in turkeys. In one such case, the oocysts are collected from the feces only during the first few hours after patency. In this manner, the prepatent time period can be progressively reduced. This type of passage is termed a selection passage. Alternatively, in order to increase the numbers of oocysts available for harvest, it may be advantageous to collect oocysts at a time between the onset of patency and the approximate prepatent time period of the parent strain. This type of passage is termed a neutral passage. Finally, in the process known as relaxed passage, virtually all of the oocysts are collected, including those produced later than the prepatent time period of the parent strain.

Vaccines

The vaccines of the present invention can be prepared by many procedures, one of which is provided solely as an example.

Composition of the Product Six turkey *Eimeria* species were isolated and then propagated by passage through turkeys.

Proportions (Viable Oocyst or Unit Per 1000 Doses)

| Species | Oocysts |
| --- | --- |
| E. adenoeides | $1 \times 10^4$-$1 \times 10^6$ |
| E. dispersa | $1 \times 10^4$-$1 \times 10^6$ |
| E. gallopavonis | $1 \times 10^4$-$1 \times 10^6$ |
| E. meleagridis | $1 \times 10^4$-$1 \times 10^6$ |
| E. meleagrimitis 1 | $1 \times 10^4$-$1 \times 10^6$ |
| E. meleagrimitis 2 | $1 \times 10^4$-$1 \times 10^6$ |

Cultures

Method of Identification: The coccidia are identified by microscopic examination and measurements of length and width. The area of infection (pathological changes) is also a criterion in distinguishing species of *Eimeria*. As each species is antigenically distinct, cross immunological studies in susceptible and unimmunized birds can also be used as a means of identification of cultures.

Glassware and utensils used in production laboratories are washed thoroughly after use and remain in their species-specific room. If such items are to be used for a different *Eimeria* species grown in the same host, they are subjected to autoclaving at 121° C. for 30 minutes and/or heat-treatment at greater than 100° F. for 72 hours or greater than 150° F. for 48 hours.

Virulence and Purity of Cultures: Purity of seed cultures may be obtained by single cell isolation. A viable oocyst, measured with an ocular micrometer, is given to 3-10 day old coccidian-free birds orally. As the prepatent period is known for each species, the bird is sacrificed at time of oocyst production and the intestines and/or cecal pouches are washed with sterile water, 2.5% potassium dichromate is added and aerated for 24-72 hours in order to allow the oocysts contained in the suspension to become sporulated, and thereby, infective. These are passed through another coccidia-free bird and the process is repeated until sufficient numbers of oocysts have been obtained which will be used as seed for production.

Composition of Media: All oocysts, obtained in pure cultures as described above, are reproduced in live poults hatched, quarantined and maintained free of coccidial infection. Birds vary in age from 3-28 days of age for seed production and from 3-8 weeks for vaccine production. The birds are checked for absence of infection by the sugar flotation method weekly and just prior to time of inoculation.

Seed cultures/Oocysts: Seed cultures are stored at refrigeration temperature. Oocysts for inoculation are suspended in cool tap water.

Inoculations: Individual birds are inoculated with 1.0 ml of the suspension by inserting a calibrated pipette or syringe containing the oocyst suspension into the crop. The number of oocysts per 1.0 ml varies with each species:

| Species | Viable Oocysts/mL |
| --- | --- |
| E. adenoeides | $1 \times 10^3$-$5 \times 10^5$ |
| E. dispersa | $1 \times 10^3$-$5 \times 10^5$ |
| E. gallopavonis | $1 \times 10^3$-$5 \times 10^5$ |
| E. meleagridis | $1 \times 10^3$-$5 \times 10^5$ |
| E. meleagrimitis 1 | $1 \times 10^3$-$5 \times 10^5$ |
| E. meleagrimitis 2 | $1 \times 10^3$-$5 \times 10^5$ |

Propagation and Harvesting of Oocysts:

Each species is propagated in the intestine of live turkeys. Following an appropriate prepatent period, see above, non-sporulated oocysts are deposited in the droppings. Droppings may be collected daily from the fourth-eleventh day after inoculation. Oocysts are examined microscopically and should conform to the size and shape of the oocysts used in the inoculation. No other types should be present, which otherwise will indicate that a contaminating species had been inadvertently introduced. Random birds may be sacrificed and observed for characteristic lesions in the appropriate sections of the intestine. No harvest is made if there is any evidence of lesions caused by extraneous disease or other species of coccidia.

| SPECIES | VIABLE OOCYSTS PER ML | PREPATENT PERIOD |
| --- | --- | --- |
| E. adenoeides | 5,000-100,000 | 104 HOURS |
| E. dispersa | 20,000-200,000 | 144 HOURS |
| E. gallopavonis | 5,000-100,000 | 144 HOURS |
| E. meleagrimitis 1 | 5,000-100,000 | 144 HOURS |

Birds used for production of each species of coccidia are reared in batteries and maintained in quarantine until needed for production. They are transferred to a room designated for the production of a species, and each bird is infected orally with a suspension of a pure seed culture of oocysts. The birds are tended to by trained technicians during the prepatent period.

The prepatent period varies with each species.

Droppings of infected birds are collected on trays containing paper which is changed daily. The droppings are transferred to a clean beaker and mixed with tap water to yield a soupy consistency. A 1:10 dilution is made of this suspension in tap water and the oocysts are counted in a hemocytometer. If the count appears high enough, the oocysts are washed out of the droppings.

If the droppings are rich in oocysts count, a 1:5 dilution (approximate) is made of the soupy suspension in 2.5% potassium dichromate and the suspension is vigorously stirred. The heavier extraneous particles settle out rapidly and the oocysts remain suspended in the supernate. This supernate is passed through a 100-mesh screen to remove any large floating particles. This procedure is repeated by washing the sediment several times in order to remove the majority of oocysts. The supernate pool is transferred to flasks and aerated by bubbling air through it. The aeration is continued for 24-72 hours until maximum sporulation has been obtained.

Following aeration, the oocysts are held at room temperature until they have settled out. The sediment is washed with 2.5% Dichromate until no oocysts can be observed in the sediment. The settling out and pouring off of supernate is repeated until the oocysts are contained in a volume which would be approximately one half sediment and one half clean Dichromate. The suspension is cooled to approximately 4° C. then cold beta-propiolactone is added at a 0.1-0.2% final concentration and placed in the cooler. Alternately, the droppings are diluted with tap water and passed through a 100-mesh screen. This procedure is repeated several times to remove the majority of the oocysts. The supernate is concentrated by allowing it to sit until the oocysts settle or by continuous flow centrifugation at 2000 RPM. The sediment is then mixed with a saturated sugar solution and centrifuged with the effluent retained.

The effluent is diluted with cool tap water and recentrifuged with the sediment containing the oocysts being retained. The oocysts are resuspended with 2.5% Potassium Dichromate and aerated for 24-72 hours. Beta-propiolactone is added at 0.1-0.2% final concentrate and placed in a cooler.

Each species suspension is cultured for sterility. One ml from each suspension is inoculated on to each of the following: Brain Heart, Desoxycholate, SS and Sabouraud's Dextrose Agar. No pathogens may be present.

Aliquots of each species with an optimum number of oocysts are inoculated orally into a groups of three 2-8 week old birds. These birds are sacrificed during the infection period to ascertain that the lesions produced were caused by the species intended. Each lot must contain only the species intended.

All discarded material is handled in accordance with V.S. Memo 800.56. Solid materials are placed in polyethylene bags and buried or incinerated. Liquids are treated with household bleach (50 ml per 1000 ml fluids to give approximately 600 ppm chlorine) and held at room temperature for at least 15 minutes prior to disposal through the sanitary sewer.

Bird cages or batteries are pressure washed and decontaminated with dry heat (150° F. for 48 hours or 100° F. for 72 hours).

Batching

Batch Assembly Example: (Average Batch 80,000 ml)

Minimum Number of Sporulated Oocysts in 2.5% Potassium Dichromate Solution

| Species | 1000 DOSE | 5000 DOSE |
|---|---|---|
| *E. adenoeides* | $4 \times 10^9$ | $8 \times 10^9$ |
| *E. dispersa* | $8 \times 10^9$ | $1.6 \times 10^{10}$ |
| *E. gallopavonis* | $4 \times 10^9$ | $8 \times 10^9$ |
| *E. meleagrimitis* 1 | $4 \times 10^9$ | $8 \times 10^9$ |
| *E. meleagrimitis* 2 | $4 \times 10^9$ | $8 \times 10^9$ |

Volume of average batch: 80,000 ml

Volume of maximum batch: 160,000 ml

Fill Volume: (Fill Volume is Checked Periodically During Filling.)

4.2±12 ml in a sterile 10 ml vial for 1,000 doses 10.5±0.5 ml in a sterile 20 ml vial for 5,000 doses The bulk vaccine is agitated during filling and dispersed into the final containers by means of a pipetting machine. The filling syringes and tubing are sterilized in an autoclave prior to use. Final containers are oven sterilized in covered pans and allowed to cool prior to filling. Rubber stoppers, sterilized in the autoclave, are placed in the vials and an aluminum seal applied. Filled vials are stored in a cooler at 3-7° C.

Adjuvants

Under certain circumstances the vaccine compositions of the present invention also can include a pharmaceutically acceptable adjuvant. Adjuvants of the present invention may be obtained from any of a number of sources including from natural sources, recombinant sources, and/or be chemically synthesized, etc Suitable adjuvants for the vaccination of animals include, but are not limited to, Adjuvant 65 (containing peanut oil, mannide monooleate and aluminum monostearate); Freund's complete or incomplete adjuvant; mineral gels, aluminum compounds such as aluminum hydroxide, aluminum phosphate, and alum; surfactants, such as hexadecylamine, octadecylamine, lysolecithin, dimethyldioctadecylammonium bromide, N,N-dioctadecyl-N',N'-bis (2-hydroxymethyl) propanediamine, methoxyhexadecylglycerol, and pluronic polyols; polyanions, such as pyran, dextran sulfate, poly IC, polyacrylic acid; peptides, such as muramyl dipeptide, dimethylglycine and tuftsin; and oil emulsions. Information concerning adjuvants is disclosed, e.g., in the series by P. Tijssen [*Practice and Theory of Enzyme Immunoassays,* 3*rd Edition*, Elsevier, New York, (1987), incorporated in its entirety by reference herein].

Other potential adjuvants include, but are not limited to metabolizable and non-metabolizable oils, block polymers, ISCOM's (immune stimulating complexes), vitamins and minerals (including but not limited to: vitamin E, vitamin A, selenium, and vitamin B12), Quil A (saponins), polymers of acrylic acid cross-linked with polyalkenyl ethers or divinyl glycol, as sold under the trademark CARBOPOL® (e.g., CARBOPOL® 941), and a uniformly dispersed micron size oil droplets in water emulsion (e.g., as sold under the trademark Emulsigen®).

Additional examples of adjuvants, that sometimes have been referred to specifically as immune stimulants, include bacterial and fungal cell wall components (e.g., lipopolysaccarides, lipoproteins, glycoproteins, muramylpeptides, beta-1,3/1,6-glucans), various complex carbohydrates derived from plants (e.g., glycans, acemannan), various proteins and peptides derived from animals (e.g., hormones, cytokines, co-stimulatory factors), and novel nucleic acids derived from viruses and other sources (e.g., double stranded RNA, CpG). In addition, any number of combinations of the aforementioned substances may provide an adjuvant effect, and therefore, can form an adjuvant of the present invention.

A vaccine of the present invention is readily administered by any standard route including spray, intravenous, intramuscular, subcutaneous, oral (including in the feed and/or drinking water), intranasal, intradermal, and/or intraperitoneal vaccination. The artisan will appreciate that the vaccine composition is preferably formulated appropriately for each type of recipient animal and route of administration.

Example 1

A New Pathogenic Species of *Eimeria*

SUMMARY

As demonstrated herein, *E. meleagrimitis* 2 (*E. edgari*) is a new, pathogenic species of coccidia for turkeys. Birds immunized with a combination of *E. adenoeides, E. meleagrimitis* 1, *E. dispersa* and *E. gallopavonis* (Coccivac-T) or *E. adenoeides* and *E. meleagrimitis* (Immucox) or *E. meleagrimitis* 1 as single entities were not protected against *E. meleagrimitis* 2. *E. meleagrimitis* 2 was isolated from commercial turkey operations from several states throughout the US and wild turkeys from the Delmarva region. Young poults hyper-immunized over several weeks with *E. meleagrimitis* 1, E adenoeides and *E. dispersa* (E.MAD) and challenged with the suspect organisms (*E. meleagrimitis* 2) exhibited clinical signs of severe parasitism (depression, off feed and lethargy) by 6.5 days post challenge. Poult-developed immunity following several low grade exposures and immunity was only to E. meleagrimitis 2.

E. meleagrimitis 2 invades the same regions of the intestines as E. meleagrimitis 1 and E. dispersa, but the oocysts of E. meleagrimitis 2 are smaller than those of these two other species. Birds immunized with E. MAD were not protected against E. meleagrimitis 2 and birds immunized with E. meleagrimitis 2 were not protected against E. meleagrimitis 1, E. adenoeides or E. dispersa. E. meleagrimitis 2 appears to be relatively prevalent in the U.S., being present in many of the U.S. turkey-growing areas. Indeed, the prevalence of E. meleagrimitis 2 is estimated to be more than 40%, with these organisms being identified in fecal samples from California, Iowa, North and South Dakotas, Minnesota, Pennsylvania, Virginia, Wisconsin, Delaware, and Maryland.

Materials and Methods

Coccidia source: Fecal samples, litter samples and or gastrointestinal samples were evaluated due to outbreaks of coccidiosis in commercial turkey flocks. The recovered organisms were originally characterized as E. meleagrimitis 1-like based on morphology, region of the gastrointestinal tract parasitized and their pathology. Samples were obtained from commercial turkey farms from the following states: California, Iowa, North and South Dakotas, Pennsylvania, Minnesota, and Virginia. Fecal samples were also obtained from wild turkeys from Delaware and Maryland.

Pathogenicity and Pathology. Parasitism with E. meleagrimitis 2 is accompanied by severe mucus production in the upper half of the small intestines and moderate to severe hemorrhage occurring from the duodenum to the ileum as the infection progressed. Gross lesions are hyperemia, excess mucus in the duodenum and jejunum, followed by hemorrhage in the mucosa in the small intestines. The feces of infected animals are watery, mucoid, and bloody. The parasites invade the epithelial cells from the duodenum to the rectum and are occasionally found in the ceca.

Tests Conducted: Anticoccidial Sensitivity Test (AST): Coccidia were expanded in naïve turkey poults and tests were conducted to determine the effectiveness of specific anticoccidials against several of the isolates. The isolates from the commercial farms showed tolerance or resistance to CLINA-COX® and AMPROL®. In the Iowa, California, Minnesota cases, there were reports of CLINACOX® failures during the usage period. As it is now known, the predominant organisms were E. meleagrimitis 1-like which herein have been disclosed and identified as E. meleagrimitis 2. The wild turkey isolates from Delaware and Maryland were tested against specific anticoccidials such as CLINACOX® and AMPROL®. The findings were similar, the drugs demonstrated poor efficacy against the isolates from wild turkey, Table 1. E. meleagrimitis 1 from Coccivac®-T demonstrated moderate tolerance to CLINACOX®, but less pronounced than the response from meleagrimitis 2.

Hyper-immunization: Young turkey poults grown in cages were given multiple inoculations over several weeks with either Coccivac™-T, a combination of E. adenoeides, E. dispersa and E. meleagrimitis 1 (Coccivac®-T) or E. meleagrimitis 1, or a combination of E. adenoides and E. meleagrimitis 2 (Immucox™), or E. meleagrimitis 2.

Inoculation methods: Poults were initially inoculated within the first seven days of age, then several times for the next several weeks. The initial inoculation was done via gavage and the subsequent inoculations were via feed. Each subsequent dose was twice the previous dose.

Challenge/Oocyst Inoculation: At approximately 28 days of age, healthy birds were selected and randomized into challenge cages. Each challenged bird was given 1 ml of a homologous or heterologous material.

Gross Lesion and Microscopic Scoring: At 6 days post-challenge, all birds were euthanized and intestines scored for lesions using a 0 to 4 system. Wet mount smears prepared from six areas of each intestine, 1) duodenum, 2) jejunum, 3) yolk stalk diverticulum (YSD), 4) ileum, 5) cecal pouch (CP) and, 6) rectum for determination of parasite burden using a 0 to 4+ system (0=no parasitism and 4=severe parasitism).

Results and Discussion

Immunization with E. MAD: Birds immunized with E. MAD and challenged with one of several heterologous materials showed that the birds were not protected against the unknown organisms herein referred to as E. meleagrimitis 2. The level of parasitism ranged from moderately severe to severe (see, Table 1).

TABLE 1

Levels of Parasitism in E. MAD Hyper-Immunized Poults Challenged with Field Isolates of E. meleagrimitis 2[A]

| Challenge | Duodenum | Jejunum | YSD | Ileum | CP | Rectum |
|---|---|---|---|---|---|---|
| E. me2-1 | +++ | +++ | ++ | ++++ | + | ++++ |
| E. me2-2 | | | | ++ | ++ | + |
| E. me2-3 | + | +++ | ++ | ++ | ++ | |
| E. me2-4 | ++++ | ++++ | ++++ | ++ | | |

[A]Field isolates had been characterized by PCR as containing E. meleagrimitis 2, as well as other Eimeria in some cases.
YSD = yolk sac diverticulum;
CP = cecal pouch;
E. me2 = E. meleagrimitis 2

Immunization with E. meleagrimitis 1: Birds immunized with E. meleagrimitis 1 and challenged with one of field isolates showed that the birds were not protected against the organism that is disclosed and defined herein as E. meleagrimitis 2. The level of parasitism ranged from moderately severe to severe (see, Table 2). However, poults challenged with homologous material showed no gross or parasite burden, (see, Table 2).

TABLE 2

Levels of Parasitism in E. meleagrimitis 1 Hyper-immunized Poults Challenged with Field isolates of E. meleagrimitis 2[A]

| Challenged | Duodenum | Jejunum | YSD | Ileum | CP | Rectum |
|---|---|---|---|---|---|---|
| E. me2-A | +++ | +++ | +++ | ++ | + | + |
| E. me2-B | +++ | ++++ | ++++ | ++++ | ++ | + |
| E. me2-C | ++ | +++ | +++ | ++ | + | |
| E. me2-D | +++ | +++ | +++ | +++ | +++ | |
| E. me2-E | +++ | +++ | ++ | + | ++ | |
| E. me2-F | + | + | ++ | ++ | + | + |
| E. me2-G | ++ | +++ | ++++ | ++++ | +++ | + |

[A]Field isolates had been characterized by PCR as containing E. meleagrimitis 2, as well as other Eimeria in some cases.
E. me2 = E. meleagrimitis 2;
YSD = yolk sac diverticulum;
CP = cecal pouch Immunization with IMMUCOX®: Birds immunized with IMMUCOX® and challenged with one of several heterologous materials including Coccivac®-T or homologous materials showed that the birds were not protected against Coccivac®-T, but provided mixed results against the unknown organisms, defined herein as *E. meleagrimitis* 2. The level of parasitism ranged from none to rare parasitic cells for *E. meleagrimitis* 2 to severe parasitism for the Coccivac®-T organisms (see, Table 3).

TABLE 3

Levels of Parasitism in IMMUCOX ® Hyper-Immunized Poults Challenged with Field Isolates of *E. meleagrimitis* 2[A] or E. MAD

| Challenge | Duodenum | Jejunum | YSD | Ileum | CP | Rectum |
|---|---|---|---|---|---|---|
| E. me2 | + | R | + | + | − | − |
| E. me2 | − | R | − | − | R | − |
| IMMUCOX ® | − | − | − | R | − | − |
| E. MAD | +++ | +++ | | +++ | ++ | + |

[A] Field isolates had been characterized by PCR as containing *E. meleagrimitis* 2 as well as other *Eimeria* in some cases.
E. me2 = *E. meleagrimitis* 2;
YSD = yolk sac diverticulum;
CP = cecal pouch;
R = Rare Immunization with *E. meleagrimitis* 2 Birds immunized with *E. meleagrimitis* 2 and challenged with one of several field isolates of *E. meleagrimitis* 2 showed that the birds were protected. The level of parasitism ranged from none to mild parasitism, but birds challenged with *E. meleagrimitis* 1 showed no protection as measured by the parasite load in the upper small intestine (see, Table 4).

TABLE 4

Levels of Parasitism in *E. meleagrimitis* 2 Hyper-Immunized Poults Challenged with Field Isolates of *E. meleagrimitis* 2[A]

| Challenged | Duodenum | Jejunum | YSD | Ileum | CP | Rectum |
|---|---|---|---|---|---|---|
| E. me2-1 | − | − | − | − | − | − |
| E. me2-2 | − | − | − | − | − | − |
| E. me2-3 | − | − | − | − | − | − |
| E. me2-4 | + | ++ | + | − | − | − |
| E. me2-5 | − | − | − | − | − | − |

[A] Field isolates had been characterized by PCR as containing *E. meleagrimitis* 2 as well as other *Eimeria* in some cases.
E. me2 = *E. meleagrimitis* 2;
YSD = yolk sac diverticulum;
CP = cecal pouch Pathogenicity and Pathology. Parasitism with this species is accompanied by severe mucus production in the upper half of the small intestines, with moderate to severe hemorrhage occurring from the duodenum to the ileum as the infection progressed. Gross lesions are hyperemia, excess mucus in the duodenum and jejunum, followed by hemorrhage in the mucosa in the small intestines, (see, Table 5 and 6, FIGS. 1 and 2).

TABLE 5

The Severity of Gross Lesions and Regions of the Intestines Affected by *E. meleagrimitis* 2 in Poults Hyper-Immunized Against *E. meleagrimitis* 1 or *E. meleagrimitis* 2

| Immunizing Species | Challenge Isolate | Upper Intestine | Middle Intestine | Lower Intestine |
|---|---|---|---|---|
| E. me1 | 1 | NA | NA | NA |
| E. me1 | E. me2-2 | 3.5 | 3.5 | 4 |
| E. me1 | E. me2-3 | 0 | 0 | 0 |
| E. me1 | E. me2-4 | 4 | 4 | 4 |
| E. me1 | E. me2-5 | 4 | 4 | 4 |
| E. me1 | E. me2-6 | 3 | 2.5 | 2 |
| E. me1 | E. me1 | 0 | 0 | 0 |
| E. me2 | E. me1 | 2.3 | 0 | 0.3 |
| E. me2 | E. me2-B | 0 | 0 | 0 |
| E. me2 | E. me2-C | 0 | 0.5 | 1 |
| E. me2 | E. me2-D | 0 | 0 | 0 |
| E. me2 | E. me2-E | 0 | 0 | 0 |
| E. me2 | E. me2-A | 0 | 0 | 0 |

E. me1 = *E. meleagrimitis* 1; E. me2 = *E. meleagrimitis* 2; NA = not applicable

TABLE 6

Severity of Gross Lesions and Oocysts Output Per Bird (OPB) in Millions for Poults Hyper-Immunized Against *E. meleagrimitis* 1 or *E. meleagrimitis* 2 and Challenged with *E. meleagrimitis* 2

| Immunizing Agent | Challenge Isolate | Lesion Scores | OPB × $10^6$ |
|---|---|---|---|
| E. me1 | 1 | NA | NA |
| E. me1 | E. me2-2 | 3.5 | 3.5 |
| E. me1 | E. me2-3 | 0 | 0 |
| E. me1 | E. me2-4 | 4 | 4 |
| E. me1 | E. me2-5 | 4 | 4 |
| E. me1 | E. me2-6 | 3 | 2.5 |
| E. me1 | E. me1 | 0 | 0 |
| E. me2 | E. me1 | 2.3 | 0 |
| E. me2 | E. me2-B | 0 | 0 |
| E. me2 | E. me2-C | 0 | 0.5 |
| E. me2 | E. me2-D | 0 | 0 |
| E. me2 | E. me2-E | 0 | 0 |
| E. me2 | E. me2-A | 0 | 0 |

E. me1 = *E. meleagrimitis* 1; E. me2 = *E. meleagrimitis* 2; NA = not applicable Summary Data from immunization and cross-immunization studies with coccidia from different sources, heterologous and the homologous species showed that poults immunized with *E. meleagrimitis* 1, *E. adenoeides* and *E. dispersa* (E. MAD) and challenged with *E. meleagrimitis* 2 were not protected against that challenge. Poults immunized against *E. meleagrimitis* 2 and challenged with *E. meleagrimitis* 2 showed a high degree of protection, but not when challenged with the *E. meleagrimitis* 1.

Oocyst Description

*Eimeria meleagrimitis* 2 (*E. edgari* sp.n.) as disclosed herein. The sporulated oocysts are subspherical, measuring 17.82×16.44 microns (16.92-19.55×14.59-18.31 microns) with a shape index of 1.084.

*E. meleagrimitis* 1. The sporulated oocysts are subspherical, measuring 21.47×19.19 microns (18.90-25.93×16.36-21.78 microns) with a shape index of 1.119. *Eimeria meleagrimitis* 1 referenced in the Diseases of Poultry: The sporulated oocysts are subspherical, measuring 19.2×16.3 microns with a shape index of 1.178.

Example 2

Cross Protection Study in Turkeys

Materials and Methods. Forty, 4 day of age commercial turkey poults were hyper-immunized over a 28 day period with a pure stock of E. meleagrimitis 1 (E. me-080121). Forty, four-day old poults (hatch-mates) were maintained coccidia-free by being fed AMPROL® at 125 ppm during the growing period. The AMPROL® was removed 96 hours prior to the challenge. Birds from the hyper-immunized and the control groups were randomized into five groups and challenged with one of five treatments, as shown in Table 1. There were seven birds per group. The turkeys were deemed ready for challenge when no oocysts were shed in feces 5 to 6 days following exposure. Challenge was performed by oral gavage and chickens were euthanized and scored for gross lesions of coccidiosis on a 0 to 4 scale (no lesions to severe lesions) on day 6 post-challenge. Cumulative gross lesion scores from the duodenum, mid gut, ileum and ceca were tabulated (Gross). The intestine was examined for microscopic parasitemia (Micros) at 100× and scored on a 0 to 4 scale. Oocyst shed was determined by collection of feces collected from each bird over a 48 hour period from day 4 to day 6. Oocysts were counted and tabulated per gram, per bird (OPB). See Table 1 for results. Gain was calculated as the difference in body weight from day of challenge and day 6.

TABLE 1

Cross Protection Study in Turkeys Immunized Against EME1 and Challenged with Various Isolates as Measured by Weight Gain and Parasite Burden

| Vaccine | Challenge | Gain (g) | Gross | Micro | OPB × $10^6$ |
|---|---|---|---|---|---|
| E. me1-080121 | E. me1-080121 | 393 | 0 | 0 | 0 |
| E. me1-080121 | E. me1-071690 | 341 | 0.14 | 0.43 | 0 |
| E. me1-080121 | E. me2-WPC | 266 | 2.99 | 8.66 | 222 |
| E. me1-080121 | E. me2-UK | 206 | 2.85 | 6.43 | 250 |
| E. me1-080121 | E. me2-Sundale | 267 | 4.6 | 10.4 | 49.2 |
| Control | E. me2-UK | 235 | 1.14 | 4.57 | 68.7 |
| Control | E. me2-WPC | 293 | 0.86 | 4.85 | 52.3 |
| Control | E. me1-071690 | 302 | 0 | 7.57 | 36.9 |
| Control | E. me1-080121 | 303 | 0 | 5.71 | 88.3 |
| Control | E. me2-Sundale | 213 | 1.25 | 7.75 | 15.0 |

E. me1-080121 = stock E. meleagrimitis 1;
E. me1-071690 = stock E. meleagrimitis 1;
E. me2-WPC = field isolate of E. meleagrimitis 2 = E. edgari;
E. me2-Sundale = field isolate of E. meleagrimitis 2 = E. edgari;
E. me2-UK = stock E. meleagrimitis 2

Results and Conclusions

Birds immunized with E.me1-080121 were solidly immune when challenged with E. me1-080121, with no gross lesions, no oocysts shed and no parasites observed in situ. Chickens immunized with E.me2-080121 showed solid immunity when challenged with E.me1-071690, with no gross lesions, no oocysts shed and no parasites observed in situ; but there were E. adenoeides parasites observed in the cecal tissue. Chickens immunized with E.me1-080121 and challenged with either E.me2-UK, E.me2-WPC or E.me2-Sundale were not protected from the challenge with E.me1 as demonstrated by growth depression, gross lesions, microscopic parasitemia and oocyst shed. All of the E.me2 isolates demonstrated pathogenicity in coccidia naïve poults. Gross pathologies were similar among the E.me2 isolates. E.me1 and E.me2 were not similar.

Example 3

Sequence Analysis of Turkey *Eimeria* Species

Four turkey *Eimeria* reference strains previously classified by examination of their pathology in birds were obtained from the University of Georgia. DNA sequence analysis was performed on cloned, PCR amplified fragments of the ITS-1 region (internally transcribed spacer one of the 18S-5.8S-28S ribosomal DNA cluster) from each strain, and phylogenic relationships were established. Whereas, analogous analyses had been performed to identify different chicken *Eimeria* isolates, heretofore, no such analysis had been performed on turkeys.

The present results identify the four turkey previously classified species, plus unexpectedly identify an additional turkey *Eimeria* species that had previously been grouped with *E. meleagrimitis* 1 (see, Example 1 above). The additional species, disclosed, characterized, and described herein, has been named *E. meleagrimitis* 2. In addition to classifying the various US turkey isolates, PCR primer sets capable of identifying each of the five species are also disclosed herein. These PCR primer sets have proved, inter alia, to be useful as diagnostic tools.

A vaccine that has long been used to aid in the prevention of turkey coccidiosis, Coccivac-T®, contains live oocysts from four species of turkey *Eimeria: E. adenoeides, E. meleagrimitis* (identified herein as *E. meleagrimitis* 1), *E. gallopavonis*, and *E. dispersa*. Previously, the nucleotide sequence of the ITS-1 region, located between the 18S and 5.8S ribosomal RNA genes in the *Eimeria* genome, has been used to establish phylogenic relationships between different species of *Eimeria* that infect chickens. Genbank contains numerous deposits of this region for various chicken isolates to support its use in speciating isolates, but there are no comparable deposits for turkey species in this specific region.

As disclosed herein, reference stocks of each known turkey *Eimeria* species were obtained from a well respected source and the ITS-1 sequence was then determined for each of the isolates obtained. A comparison was performed between the sequences of the reference stocks and those contained in Coccivac-T®. In addition, an analysis of the phylogenetic tree was performed. The sequence analyses were also used to determine whether primer sets based on the four previously classified turkey species could unequivocally identify all of the various isolates.

Materials and Methods

Commercial Kits and Gels: see Table 1

TABLE 1

Kits and Gels

| REAGENT | MANU-FACTURER | CATALOG/PART NO. | PROCEDURE |
|---|---|---|---|
| QIAamp DNA Mini Kit | Qiagen | 51304 | *Eimeria* DNA extraction |
| HotStar Taq Master Mix Kit | Qiagen | 203444 | PCR amplification |
| E-Gels | Invitrogen | G5018-02 | Visualizing PCR fragment |
| QIAquick Gel Extraction Kit | Qiagen | 28704 | PCR product purification from agarose |
| TOPO TA Cloning Kit | Invitrogen | K4400-40 | Cloning PCR fragment |
| QIAprep Spin Miniprep Kit | Qiagen | 27104 | Extracting DNA from bacteria containing cloned PCR fragment |

Biological Products: Reference *Eimeria* samples (see Table 2) were obtained from the University of Georgia, at Athens (UGA). All UGA *Eimeria* isolates had previously been characterized by pathology. Some of the samples were from field isolations, and therefore, potentially contained multiple species.

The DNA was also isolated from the species in the Coccivac-T® turkey *Eimeria* vaccine, which contains isolates of *E. adenoeides, E. meleagrimitis, E. dispersa* and *E. gallopavonis*. In addition, DNA and sequence information from three European turkey *Eimeria* samples were obtained. These samples had been characterized by pathology, and were labeled *E. adenoeides*-EU, *E. dispersa*-EU and *E. meleagrimitis* 1-EU.

Figure 3B:
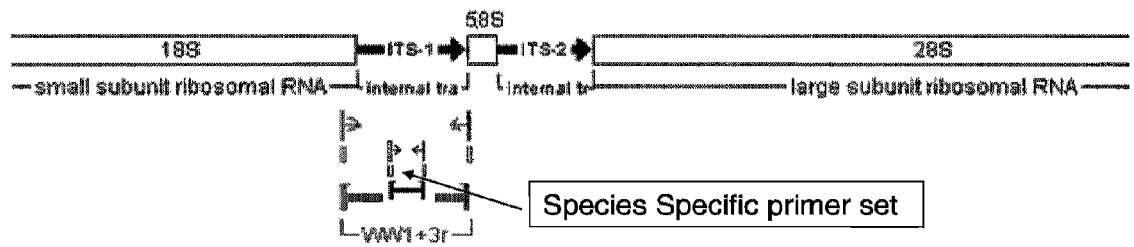
FIG. 3B shows the location of Internal Species Specific Primers.

Protocol:
- DNA was isolated from the UGA reference turkey *Eimeria* samples (see, Table 2).
- The ITS-1 region(s) of each reference strain was amplified by PCR using WW1/WW3r primer set for ITS-1 amplification and then purified [see, Table 5 for primer sequence, and FIG. 3A for their location on genome; Woods et. al. *Electrophoresis* 21:3558-3563 (2000)].
- Each PCR fragment was cloned into a plasmid vector, pCR2.1-TOPO, and the fragment is sequenced.
- The sequence data was analyzed by a commercially available program, [DNASTAR analysis software, Seqman, Editseq, Mapdraw, Megalign] and phylogenic relatedness of reference strains to in-house strains was determined (see, FIG. 4).
- Discrepancies were evaluated between the species determinations obtained by the pathology and by sequence analysis using PCR amplification employing internal ITS-1 species primer sets (see, Table 5 for primer sequences, FIG. 3B for location on genome, and Table 7).

Experimental Procedures

Sucrose Purification of Oocysts—RDP 7416.0-01 (Manual/Small Scale)

Excystation of Sporocysts—RDP 7423.0-01
- Suspend 1×10e5 to 1×10e6 oocysts in 1 mL of PBS, using a 1.5 mL snap-cap microfuge tube and add one gram clean (sterile) glass ballotini [SIGMA 710-1, 180 µm (16-25 U.S. sieve)] to the tube. Close the cap.
- Vortex on highest setting for 1 minute, then transfer the sporocyst suspension by pipetting to a 2 mL microfuge tube, and rinse the beads with more PBS to q.s. to 2 mL.
- Centrifuge the sporocyst suspension (12,000 r.p.m. for 15 seconds in a microfuge), remove the supernatant, and resuspend the released sporocysts in 200 µL PBS.

DNA Extraction of Released Sporocysts is performed as described in the Qiagen QIAamp DNA mini kit (Blood and Body Fluid Spin Protocol):
- Pipet 20 µL Proteinase K into the bottom of a 1.5 mL microfuge tube.
- Add 200 µL sample to the tube, add in 200 µL Buffer AL to sample, mix by pulse vortexing for 15 seconds.
- Incubate at 56° C. for 10 minutes.
- Centrifuge briefly to remove drops from inside the lid, add 200 µL ethanol and mix again for 15 seconds. Centrifuge briefly to remove drops from inside lid.
- Transfer mixture to the QIAamp spin column, cap and centrifuge at 8000 rpm for 1 minute, transfer column to a clean 2 mL tube, discard flow-through.
- Add 500 µL Buffer AW1, cap and centrifuge at 8000 rpm for 1 minute, transfer column to a clean 2 mL tube, discard flow-through.
- Add 500 µL Buffer AW2, cap and centrifuge at 14,000 rpm for 3 minutes, transfer column to a clean 1.5 mL tube, discard flow-through.
- Add 200 µL Buffer AE, cap, incubate at room temp for 1 minute, and centrifuge at 8,000 rpm for 1 minute to collect the eluted DNA.

PCR Amplification of ITS-1
- Set up PCR reactions containing 10 µL template DNA, 1 µM each of Woods ITS-1 forward and reverse primers (WW1 and WW3r), 1× HotStar Taq Master Mix, and RNase-free water to a final volume of 50 µL. The cycling conditions were as follows: 1 cycle of 95° C. for 15 minutes; 35 cycles of 95° C. for 30 seconds, 55° C. for 30 seconds, 72° C. for 30 seconds; then 1 cycle of 72° C. for 7 minutes, followed by a 4° C. hold. A positive control DNA template and a water (no template) negative control were included for each primer set.

Electrophoresis of PCR Products—RDP 7605.0-03
- Post amplification, 10 µL of each reaction was loaded onto a 2% agarose E-Gel, and current applied for 15-30 minutes. Complete description of the use of E-Gels is described in the Invitrogen E-Gel Technical Guide. These gels contain ethidium bromide that binds to any DNA fragments, and allows them to be visualized and photographed when exposed to UV light. A 1-kb DNA ladder was run on each gel for PCR fragment size comparison.
- To purify PCR fragments, a 2% agarose gel was prepared in a solution of 1×TAE buffer and 0.5 µg/mL Ethidium Bromide, following guidelines described in RDP 7605.0-03. The remainder of the PCR reaction mix, ~40 µL, was mixed with 10× Bluejuice loading dye to a final concentration of 1×, then loaded into wells of the gel, and current applied and electrophoresed until good separation of all fragments was obtained (85V for 60 minutes, followed by 75V for 50 minutes.) Again, a 1-kb DNA ladder was also loaded as a size reverence. The gel was exposed to UV light to visualize the DNA fragments.

Gel Purification of PCR Products
- Once each PCR fragment had been separated by electrophoresis on 2% agarose, a scalpel was used to excise a block of agarose gel containing the PCR fragment, and the gel block was transferred to a weighed microcentrifuge tube.
- The volume of the gel block was determined by weight (1 milligram equals 1 µL melted gel).
- DNA was extracted using a Qiagen Gel Extraction Kit, following manufacturers instructions, and eluting DNA in a final volume of 200 µL.

Cloning PCR Products into pCR2.1-TOPO Cloning Vector, and Transformation of Plasmid into *E. Coli*.
- To clone each purified PCR fragment, follow manufacturers instruction supplied with TOPO TA Cloning KIt, including transformation of Top 10 *E. coli* competent cells.
- Plate transformed cells on imMedia Amp Agar plates, spread with 40 µL of a 40 mg/mL solution of X-Gal and incubate at 37° C. overnight.

Growth, DNA Extraction and Restriction Analysis of Clones
- After 20-24 hours bacterial growth on the transformation plates, white and blue colored bacterial colonies are visible.
- Two "white" colonies from each transformation were chosen for growth and analysis. Each colony was picked with a sterile toothpick and inoculated into 3 mL of Luria broth containing 100 μg/mL of carbenicillin antibiotic. Each culture tube was then aerated at 200 rpm at a temperature of 37° C. for approximately 16-20 hours.

DNA was extracted from 1.5 mL of each overnight culture using a Qiagen QIAprep Spin Miniprep Kit. Manufacturer instructions were followed, and DNA was eluted in a final volume of 50 μL.

Restriction digestion of each DNA prep was performed with EcoRI enzyme, and the digested material loaded onto a 1.5% agarose gel in 1×TAE buffer and 0.5 μg/mL ethidium bromide. Each digestion reaction contained 5 μL miniprep DNA, 100 μg/mL BSA, 1× EcoRI enzyme buffer, 10 U enzyme and water in a final volume of 20 μL. Reaction mixtures were incubated for greater than 2 hours at 37° C., then loading dye added to a final concentration of 1%. Next the mixture was loaded onto the gel and electrophoresed at 95V for 41 minutes. UV light was used to visualize the digestion products. Digested DNA from bacterial clones containing the desired PCR fragment released the fragment from the remainder of the plasmid and could be identified by comparison to a DNA size standard.

Sequence Analysis of Cloned PCR Products

Purified DNA from each clone containing the desired PCR fragment was sent to SeqWright DNA Technologies for Big Dye Sequence reactions using sequencing primers that anneal to the plasmid vector, and read into the cloned PCR fragment.

PCR Identity Testing Using ITS-1 Based Primer Sets

Set up PCR reactions containing 10 μL template DNA, 1 μM each of the species specific forward and reverse primers, 1× HotStar Taq Master Mix, and RNase-free water to a final volume of 50 μL. The cycling conditions were as follows: 1 cycle of 95° C. for 15 minutes; 35 cycles of 94° C. for 30 seconds, variable annealing temperature (55-65° C.) for 30 seconds, 72° C. for 30 seconds; then 1 cycle of 72° C. for 7 minutes, followed by a 4° C. hold. Reactions containing *E. adenoeides* or *E. meleagrimitis* 2 primer sets used an annealing temperature of 60° C. Reactions containing *E. dispersa* or *E. gallopavonis* primer sets used an annealing temperature of 65° C., and reactions containing the *E. meleagrimitis* 1 primer set used an annealing temperature of 55° C. A positive control DNA template and a water (no template) negative control were included for each primer set, and the results visualized as described above.

Data Analysis

Test Validity and Acceptability Criteria: ITS-1 region PCR product(s) were amplified for all isolates. Number and sequence of ITS-1 region(s) for each pure isolate were grouped into families. Isolates containing multiple species were identified based on PCR analysis with species specific primer sets.

Results

DNA was successfully extracted from all UGA turkey *Eimeria* isolates. PCR amplification of the ITS-1 region(s) was performed on each UGA isolate, along with the other US isolates (except *E. dispersa*), and the resulting fragments were cloned into a commercial plasmid to facilitate sequencing. The ITS-1 region of the internal *E. dispersa* isolate was amplified, but not cloned or sequenced, as it was identifiable using primers based on the *E. dispersa*-EU sequence. A single clone for each cloned ITS-1 fragment was sent to a commercial sequencing company [SeqWright DNA Technology Services of Houston, Tex.] to perform BigDye primer extension sequencing. Both sense and anti-sense strands were sequenced for each fragment, and the raw data was then analyzed using DNASTAR software. The analysis demonstrated unambiguous sequences for all clones.

TABLE 2

ITS-1 PCR Products of the UGA Turkey Isolates

| Isolate No. (544) | Identification | ITS-1 PCR Products (WW1/WW3r primers) |
| --- | --- | --- |
| -064A | E. dispersa | 405 bp |
| -064B | E. dispersa | 409 bp |
| -064C | E. dispersa | 409 bp |
| -065A | E. meleagrimitis 1 | 405 bp |
| -065B | E. gallopavonis | 534 bp + 392 bp |
| -065C | E. gallopavonis | 534 bp + 392 bp |
| -066A | E. adenoides | 500 bp + 417 bp |
| -066C | E. adenoides | 534 bp + 417 bp |
| -066D | E. adenoides unknown | 417 bp |
| -066E | E. adenoides | 417 bp |
| -067A | E. meleagrimitis 1 | 502 bp |
| -067B | E. meleagrimitis 1 | 503 bp |
| -067C | E. meleagrimitis 1 | 405 bp |
| -067D | E. meleagrimitis 1 | 405 bp |
| -067E | E. meleagrimitis 1/E. adenoides | 405 bp |
| -067F | E. meleagrimitis 1 (may not be pure) | 405 bp |
| -067G | E. meleagrimitis 1 | 407 bp |
| -068A | E. meleagrimitis 1 | 501 bp |

TABLE 3

Isolates from COCCIVAC-T ®

| Type | Abbrev. | ITS-1 PCR Products (WW1/WW3r primers) |
| --- | --- | --- |
| E. adenoeides | CAD | 418 bp |
| E. meleagrimitis 1 | Eme | 402 bp |
| E. dispersa | Edi | ~400 bp |
| E. gallopavonis | Ega | 535 bp + 392 bp |

TABLE 4

EU isolates

| Type | ITS-1 PCR Products (WW1/WW3r primers) |
| --- | --- |
| E. gallopavonis | 535 bp + 392 bp |
| E. meleagrimitis 2 | >500 bp |
| E. dispersa | 410 bp |

TABLE 5

PCR Primers

| Target | Primer Pair Sequences (5'→ 3') | PCR Product Size (bp) |
|---|---|---|
| ITS-1 region[a] | AAGTTGCGTAAATAGAGCCC SEQ ID NO: 1 CAAGACATCCATTGCTGAAA SEQ ID NO: 2 | variable by species ~440-770 bp may produce multiple bands |
| E. meleagrimitis 1[b] | CTCTCCTCCGTTCACTCCTTTCTG SEQ ID NO: 3 AGCCACCTGCGCAACACATTCT SEQ ID NO: 4 | 205 bp |
| E. adenoeides | GCTTGTAGGTTTGCATTGGTTC SEQ ID NO: 5 CTCGTTGTGAGAAAAGAAAAAAGAT SEQ ID NO: 6 | 172 bp |
| E. gallopavonis | TCCGTTTGTTGATTGTTGTGG SEQ ID NO: 7 TCCCCTATCAGCACCAACAAA SEQ ID NO: 8 | 282 bp |
| E. dispersa | CAGGAGCTGGTATTCATTCATTTCT SEQ ID NO: 9 AGGGCGCAACTTTCATTCTTT SEQ ID NO: 10 | 179 bp |
| E. meleagrimitis 2 (based on EU meleagrimitis)[c] | CTGGAAAGGTGCCTGTTTGT SEQ ID NO: 11 AGCACAGTGAAGCAGCTGAA SEQ ID NO: 12 | 225 bp |

Figure 4:
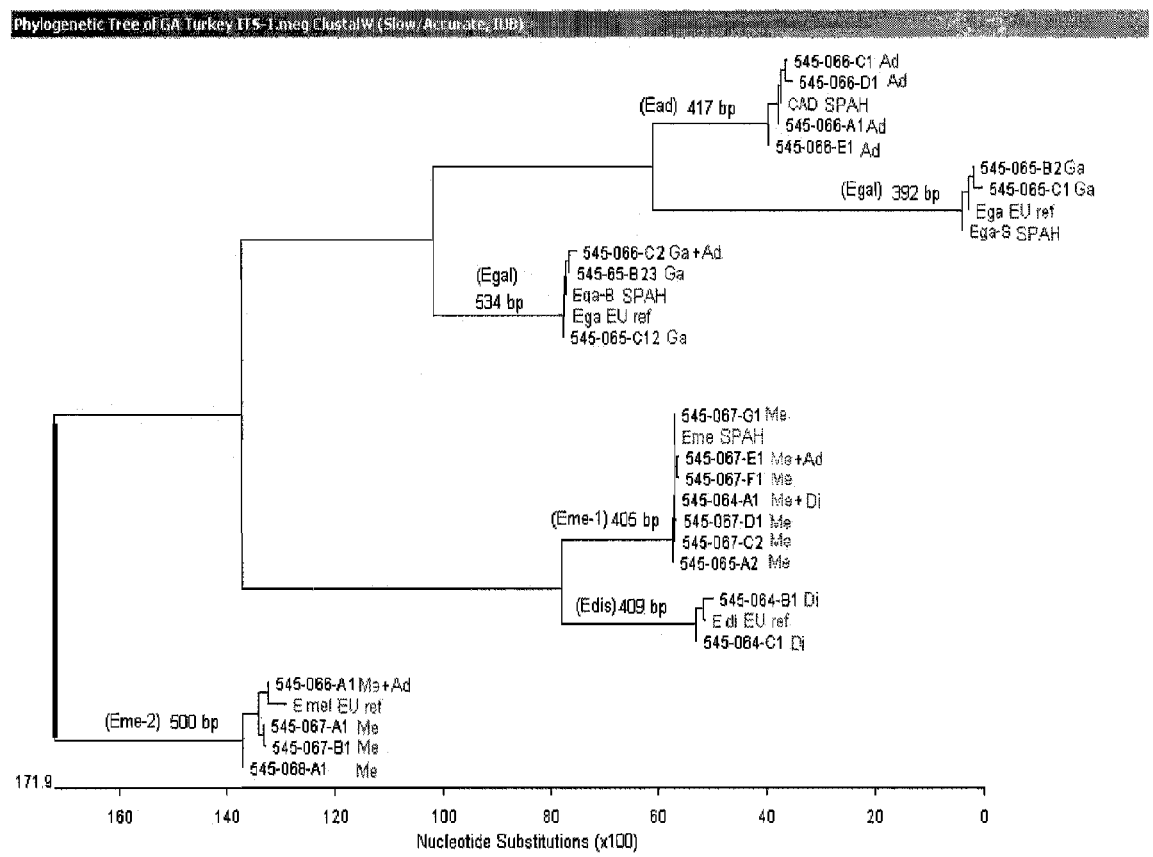
FIG. 4 shows a phylogenetic tree constructed pursuant to the present invention.

[a]Seq. Source: Woods et.al., Electrophoresis 21:3558-3563 (2000)
[b]Seq. Source: SPAH US for E. meleagrimitis 1, E. adenoeides, E. gallopavonis, and E. dispersa
[c]Seq. Source: SPAH UK Once the sequence of each ITS-1 fragment had been determined, alignment and phylogenic analysis was performed on these sequences, as well as on the sequences of the European isolates. Results of the phylogenic analysis are shown in FIG. 4. The sequence alignment analysis grouped the twenty-five isolates into five "species." E. adenoeides templates amplify a single 419 base pairs (bp) PCR product using the Woods ITS-1 primer set. E. dispersa templates yield a single 409 bp ITS-1 product. All E. gallopavonis templates produce two products, 534 bp and 392 bp in size. DNA from isolates originally characterized as E. meleagrimitis amplify a single product with the Woods primers, but surprisingly, isolates segregated into two distinct families. The ITS-1 fragments produced from these two families are different sizes and only share 10.6% homology. One family amplified a 405 bp product, whereas the second, designated E. meleagrimitis 2, amplified a 500 bp product. Sequences of the ITS-1 fragments within each group share between 96% to 100% homology, but between groups only share 10.6% to 49.7% homology.

TABLE 6

| Name | ITS-1 fragment(s) | Lot Nos. |
|---|---|---|
| E. dispersa | 409 bp | -064B, -064C Edi (Coccivac-T) Edi (UK) |
| E. adenoeides | 417 bp | -066A, -066C -066D, -066E CAD (Coccivac-T) |
| E. gallopavonis | 534 bp + 392 bp | -65B, -65C Egal(Coccivac-T) Ead (UK) |

TABLE 6-continued

| Name | ITS-1 fragment(s) | Lot Nos. |
|---|---|---|
| E. meleagrimitis 1 | 405 bp | -67C, -67D -67E, -67F -67G, -65A -64A, Eme (Coccivac-T) |
| E. meleagrimitis 2 | 500 bp | -067A, -67B -68A Eme (UK) |

With a few important exceptions, sequence-based groupings of the UGA reference strains matched pathology-based groupings. As understood from the start, not all isolates studied were pure, and by examining sequence from a single cloned fragment per isolate, there remained the possibility that some stocks contained multiple species, and that a clone of an Eimeria contaminant might be picked within a characterized stock. To determine if this might be the case where a conflict existed between the sequence information and the pathology-based characterization, a PCR analysis was performed using the species specific primers.

Finally, PCR primers that had been designed based on the EU E. meleagrimitis sequence segregated, as disclosed herein as E. meleagrimitis 2, so these primers were synthesized and used in a PCR assay, as well (see, Table 5).

PCR analysis with the species specific primers gave the following results: UGA E. adenoeides isolate 544-066A was positive with both E. adenoeides and E. meleagrimitis 2 primers. UGA E. adenoeides isolate 544-066C was positive with both E. adenoeides and E. gallopavonis primers. UGA E. dispersa isolate 544-064A was positive with both E. dispersa and E. meleagrimitis 1 primers.

TABLE 7

PCR Analysis Using Species Specific Primers to Resolve Conflicts

| Stock | PCR results (positives) | Determination |
|---|---|---|
| UGA E. adenoeides isolate | Both Eimeria adenoeides & Eimeria meleagrimitis 1 2 | Contaminated with Eimeria meleagrimitis 2 |
| UGA E. adenoeides isolate | Both Eimeria adenoeides & Eimeria gallopavonis | Contaminated with Eimeria gallopavonis |
| UGA E. dispersa isolate | Both Eimeria meleagrimitis 1 & Eimeria dispersa | Contaminated with Eimeria meleagrimitis 1 |

CONCLUSIONS

Turkey *Eimeria* isolates were studied to increase the understanding of the phylogenic relationships between the existing species, and to validate a PCR-based species identity test for the turkey isolates. Reference samples of all the known US turkey *Eimeria* strains were obtained from a collection at the University of Georgia, at Athens (UGA), and their DNA was extracted. This DNA was then subjected to PCR amplification using Woods ITS-1 region primer set, and the resulting fragments were cloned and sequenced. Phylogenetic analysis of the sequences was then performed, and the results compared with in-house isolates of turkey *Eimeria*, plus three European isolates. From these analyses, a fifth distinct species was identified. Four turkey species had been previously recognized, based on lesion pathology, but the present sequence analysis indicates that one of the four, *E. meleagrimitis* should be further subdivided into two separate species, *E. meleagrimitis* 1 and *E. meleagrimitis* 2.

Addendum

Additional PCR primers were also created based on the ITS-1 sequence of the EU turkey *Eimeria* isolates, and an "unknown" ITS-1 sequence originally amplified from Coccivac-T®. The identity of these stocks was verified in the experiment described above. These additional primers proved useful to identify the stocks described below.

TABLE 8

Additional PCR Primers

| Target | Primer Pair Sequences (5'→ 3') | PCR Product Size (bp) |
|---|---|---|
| E. gallopavonis | (5')-AGCATGAAAGCAGGGAAAGA SEQ ID NO: 45<br>(5')-TGTAACGGCTATGGGTCCTC SEQ ID NO: 46 | 347 bp |
| E. adenoeides | (5')-AGCGTCTCTTTCTTTGACTGC SEQ ID NO: 47<br>(5')-TGGTACATACACAGCCAGCAA SEQ ID NO: 48 | 151 bp |
| E. dispersa (based on EU isolate) | (5')-GTGTGAAATGGCACAGATGG SEQ ID NO: 49<br>(5')-TACAAATGCGGCTCTCAATG SEQ ID NO: 50 | 185 bp |

Example 3

Consensus Sequence for the ITS-1 Region of the 18S Ribosomal Gene of *E. meleagrimitis* 2

DNA from eight field isolates of turkey *Eimeria* was isolated and their ITS-1 regions, located between the 18S and 5.8S ribosomal genes, were PCR amplified and cloned into an *E. coli* vector. Up to five clones from each isolate (a through e), were selected and sequenced. The ITS-1 region sequences from each clone were then compared with *E. meleagrimitis* 2 reference sequences from the EU-E.me2 isolate and four UGA-E.me2 isolates. Each sequence extends from the first base after the 18S Ribosomal RNA gene to the 5.8S Ribosomal RNA gene. A phylogenetic tree was developed. The sequences were analyzed for similarity and a consensus sequence was generated (SEQ ID NO: 44, see below). The sequence includes "N's" where there are substitutions, insertions or deletions. The size range for the ITS-1 sequences among the eight isolates is 394-398 bases. The consensus sequence, SEQ ID NO: 44, shares 87.2-88.5% homology with the sequenced Eme2 ITS1 clones, as compared to the sequence homology of the eight sequences to each other which show 93.8-100% homology.

Sequence Determinations

SEQ ID NOs. 13-44 refer to the nucleotide sequences of the respective ITS-1 regions and are denoted in Full Caps. SEQ ID NOs. 51-81 refer to the entire nucleotide sequence presented.

The sequences shown BELOW do not include all 18S and 5.8S sequences that make up PCR fragment generated by Woods WW1/WW3r primer sets.

Text in BOLD is 18S region (WW1 primer is underlined)
Text in ITALICS is 5.8S region (primer WW3R is underlined)

UGA *E. gallopavonis* Isolates 544-065B: Large fragment 5'→ 3' (534 bp);
SEQ ID NO: 51
[SEQ ID NO: 13 is the ITS-1 region, displayed in Full Caps]
aagttgcgtaaatagagccctctaaaggatgcaaaagtcgtaacacgg tttccgtaggtgaacctgcggaaggatcattcACACGTAAAGCATGAA
AGCAGGGAAAGATACTTTTTGATCTTATCCGTTTGTTGATTGTTGTGG
GACAGTCAGCTTGCATGAGGGTTGGGTCACGAGTGTCTGCTGCTGTTC
AGGCTTATCCGGGTGGGACAAAGATTAACAACAACCTGTAAATCTGTT
TTTTTCTCACAACGAGTTTTCTTTTTTTTGCCGAAAAAGTCTTTTTGC
TGCTTCACTGTGTAGTGCGGTGTGGGTGTGGCGGCAGGTGTTGTGATC
TCCATAACTCCCCTCCCATGCATCATCATGACCAGTGTTGGGTACTGG
TTTGTTGGTGCTGATAGGGGAACGTTATGTAGAGGACCCATAGCCGTT
ACACAACGTTTCCGGCCTCAGTGTATTGCAGGGACTTTATTCTGTATA
TACTAACAGAATGTATATATGAAGCCAAAaaaac*tttcagcaatggat gtcttg*

544-065B: Small fragment 5'→ 3' (392 bp)
SEQ ID NO: 52
[SEQ ID NO: 14 is the ITS-1 region, displayed in Full Caps]
aagttgcgtaaatagagccctctaaaggatgcaaaagtcgtaacacgg tttccgtaggtgaacctgcggaaggatcattcACACGTATAAGCATG
AAAGCAGGAAGAGACATATTTCTTTTATTTGATCTCCTCCTATATCCT
TCTTGAGAGATCTGCGTTTACGCGGCTTGATCAAGTTTGGTGGTGGTT
GGTCAATAGAAGAGGTGTCTTTTTGACTGGTCTTTTCAGGCTTATTAT
GGGATAATATTCAACCGCAACCTGTAAATCTCTTTTTCCTCTCTCACA
ACAACGAGTTTTCTGTAGATTGCAATTGATGCAAGTGTATTCTGTACG
CTACAGAATATAAAGGTACAAAAAGAAAAAAaaaac*tttcagcaatgg atgtcttg*

-continued 544-065C: Large fragment 5'→ 3' (534 bp: 518 bp sequenced)
SEQ ID NO: 53
[SEQ ID NO: 15 is the ITS-1 region, displayed in Full Caps]
aagttgcgtaaatagagccctctaaaggatgcaaaagtcgtaacacgg
tttccgtaggtgaacctgcggaaggatcattcACACGTAAAGCATGAA
AGCAGGGAAAGATACTTTTTGATCTTATCCGTTTGTTGATTGTTGTGG
GACAGTCAGCTTGCATGCGGGTTGGGTCACGAGTGTCTGCTGCTGTTC
AGGCTTATCCGGGTGGGACAAAGATTAACAACAACCTGTAAATCTGTT
TTTTTCTCACAACGAGTTTTCTTTTTTTTGCCGAAAAAGTCTTTTTGC
TGCTTCACTGTGTAGTGCGGTGTGGGTGTGGCGGCAGGTGTTGTGATC
TCCATAACTCCCCTCCCATGCATCATCATGACCAGTGTTGGGTACTGG
TTTGTTGGTGCTGATAGGGGAACGTTATGTAGAGGACCCATAGCCGTT
ACACAACGTTTCCGGCCTCAGTGTATTGCAGGGACTTTATTCTGTATA
TACTAACAGAATGTATATATGAAGCCAAAaaaactttc 544-065C: Small fragment 5'→ 3' (392 bp)
SEQ ID NO: 54
[SEQ ID NO: 16 is the ITS-1 region, displayed in Full Caps]
aagttgcgtaaatagagccctctaaaggatgcaaaagtcgtaacacgg
tttccgtaggtgaacctgcggaaggatcattcACACGTATAAAGCATG
AAGCAGGAAGAGACATATTTCTTTTATTTGATCTCCTCCTATATCCTT
CTTGAGAGATCTGCGTTTACGCGGCTTGATCAAGTTTGGTGGTGGTTG
GTCAATAGAAGAGGTGTCTTTTTGACTGGTCTTTTCAGGCTTATTATG
GGATAATATTCAACCGCAACCTGTAAATCTCTTTTTCCTCTCTCACAA
CAACGAGTTTTCTGTAGATTGCAATTGATGCAAGTGTATTCTGTACGC
TACAGAATATAAAGGTGCAAAAGAAAAAaaaactttcagcaatgga
ttcttg 544-066C: Large fragment 5'→ 3' (532 bp)
SEQ ID NO: 55
[SEQ ID NO: 17 is the ITS-1 region, displayed in Full Caps]
aatgcgtaaatagagccctctaaaggatgcaaaagtcgtaacacgtt
tccgtaggtgaacctgcggaaggatcattcACACGTAAAGCATGAAAG
CAGGGAAAGATACTTTTTGATCTTATCCGTTTGTTGATTGTTGTGGGA
CAGTCAGCTTGCATGCGGGTTGGGTCACGAATGTCTGCTGCTGTTCAG
GCTTATCCGGGTGGGACAAAGATTAACAACAACCTGTAAATCTGTTTT
TTTCTCACAACGAGTTTTCTTTTTTTTGCCGAAAAAGTCTTTTTGCTG
CTTCACTGTGTAGTGCGGTGTGGGTGTGGCGGCAGGTGTTGTGATCTC
ACATAACTCCCCTCCCATGCATCATCATGACCAGTGTTGGGTCTGGTT
CTGTTGGTGTGATAGGGGAACGTTATGTAGAGGACCCATAGCCGTTAC
TACAACGTTTCCGGCCCAGTGTATTGCAGGGACTTTATTCTGTATATA
CTAACAGAATGTATATATGAAGCCAAAaaaactttcagcaatggatgt
cttg UGA *E. adenoeides* Isolates 544-066A: Small fragment 5'→ 3' (417 bp)
SEQ ID NO: 56
[SEQ ID NO: 18 is the ITS-1 region, displayed in Full Caps]
aagttgcgtaaatagagccctctaaaggatgcaaaagtcgtaacacgg
tttccgtaggtgaacctgcggaaggatcattcACACGTGAAGCATGAA
GGCAGAGAAAGGATGCTTTTGATCAGATATATCTGCTTTGCTTGTAGG
TTTGCATTGGTTCTTGGTAACAAGTCGCCAAGCAGATTTGCATGCATG
CAGTTTTGTGATCATTATTTATAGCGTCACTTTCTTTGACTGCTGTTT
ATGCTTTTGTTATGGATTGGACACACATTACAAAATCTGTAAATCTTT
GTTTCTTTTCTCACAACGATTTTCTCTTTGAAATTTCTGGAAAGAAAG
AATATAGATTGCTGGCTGTGTATGTACCAGCAGAATGTGTAGAATGAA
AAAGTTGAAaaaactttcagcaatggatgtcttg 544-066C: Small fragment 5'→ 3' (417 bp)
SEQ ID NO: 57
[SEQ ID NO: 19 is the ITS-1 region, displayed in Full Caps]
aagttgcgtaaatagagccctctaaaggatgcaaaagtcgtaacacgg
tttccgtaggtgaacctgcggaaggatcattcACACGTGAAGCATGA
AGGCAGAGAAAGGATGCTTTTGATCAGATATATCTGCTTTGCTTGTAG
GTTTGCATTGGTTCTTGGTAACAAGTCGCCAAGCAGATTTGCATGCAT
GCAGTTTTGTGATCATTATTTATAGCGTCACTTTCTTTGGCTGCTGTT
TATGCTTTTGTTATGGATTGGACACACATTACAAAATCTGTAAATCTT
TTTTCTTTTCTCACAACGAGTTTTCTCTTTGAAATTTCTGGAAAGAAA
GAATATAGATTGCTGGCTGTGTATGTACCAGCAGAATGTGTAGAATGA
AAAAGTTGAaaaactttcagcaatggatgtcttg 544-066D: 5'→ 3' (417 bp)
SEQ ID NO: 58
[SEQ ID NO: 20 is the ITS-1 region, displayed in Full Caps]
aagttgcgtaaatagagccctctaaaggatgcaaaagtcgtaacacgg
tttccgtaggtgaacctgcggaaggatcattcACACGTGAAGCATGAA
TGCAGAGAAAGGATGCTTTTGATCAGATATATCTGCTTTGCTTTGCAT
TGGTTCTTGGTTAGGTAACAAGTCGCCAAGCAGATTTGCATGCATG
CAGTTTAGTGATCATTATTTATAGCGTCTCTTTCTTTGACTGCTGTTT
ATGCTTTTGTTATGGATTGGACACACATTACAAAATCTGTAAATCTTT
TTTCTTTTCTCACAACGAGTTTTCTCTTTGAAATTTCTGGAAAGAAAG
AATATAGATTGCTGGCTGTGTATGTACCAGCAGAATGTGTAGAATGAA
AAAGTTGAaaaactttcagcaatggatgtcttg 544-066E: 5'→ 3' (416 bp)
SEQ ID NO: 59
[SEQ ID NO: 21 is the ITS-1 region, displayed in Full Caps]
aagttgcgtaaatagagccctctaaaggatgcaaaagtcgtaacacgg
tttccgtaggtgaacctgcggaaggatcattcACACGTGAAGCATGAA
TGCAGAGAAAGGATGCTTTTGATCAGATATATCTGCTTTGCTTGTAGG
TTTGCATTGGTTCTTGGTAACAAGTCGCCAAGCAGATTTGCATGCATG
CAGTTTTGTGATCATTATTTATAGCGTCTCTTTCTTTGACTGCTGTTT
ATGCTTTTGTTATGGGTTGGACACACATTACAAAATCTGTAAATCTTT
TTTCTTTTCTCACAACGAGTTTTCTCTTTGAAATTTCTGGAAAGAAAG
AATATAGATTGCTGGCTGTGTATGTACCAGCAGAATGTGTAGAATGAA
AAAGTTGAaaaactttcagcaatggatgtctt UGA *E. dispersa* Isolates 544-064B: 5'→ 3' (409 bp)
SEQ ID NO: 60
[SEQ ID NO: 22 is the ITS-1 region, displayed in Full Caps]
aagttgcataaatagagccctctaaaggatgcaaaagtcgtaacacgg
tttccgtaggtgaacctgcggaaggatcattcACACATTCTGTCCAAC
GGAGCTGGTATTCATTCATTTCTGTGTGAAATGGCATAGATGGGTGTT
GCAAGCTTCCTGTCTTGGGCGGCTGAGTATTGAACCTTTTTATCCCTC
CCACAACCTTTGAATCGGTTTGTTGAGTTTTCTTTCCACGACGAGTTT
TCTTAATATTTAAAAGAATGAAAGTTGCGCCCTTGCTGGCCACTCATT
GAGAGCCGCATTTGTAACTGCTCTCGTGAGCAGTGGAAGCGGGGCTTT
TTCAGTGAGTGGCTGCATGCGCGCATGCGTAATATTTATCAGCTCTTa
aaactttcagcaatggatgtcttg 544-064C: 5'→ 3' (409 bp)
SEQ ID NO: 61
[SEQ ID NO: 23 is the ITS-1 region, displayed in Full Caps]
aagttgcgtaaatagagccctctaaaggatgcaaaagtcgtaacacgg
tttccgtaggtgaacctgcggaaggatcattcACACATTCTGTCCAAC
AGGAGCTGGTATTCATTCATTTCTGTGTGAAATGGCACAGATGGGTGT
TGCAAGCTTCCTGTCTTGGGCGGCTGAGTATTGAACCTTTTTATCCCT
CCCACAACCTTTGAATCGGTTTGTTGAGTTTTCTTTCCACGACGAGTT
TTCTAAAATTTAAAAGAATGAAAGTTGCGCCCTTGCTGGCCACTCAT
TGAGAGCCGCATTTGTAACTGCTCTCGAGAGCAGTGGAAGCGGGGCTT
TTTAGGTGAGTGGCTGCATGCGCGCATGCGTAATATTTATCAGCTCTT
aaaactttcagcaatggatgtcttg UGA *E. meleagrimitis* 1 Isolates 544-067C: 5'→ 3' (405 bp)
SEQ ID NO: 62
[SEQ ID NO: 24 is the ITS-1 region, displayed in Full Caps]
aagttgcgtaaatagagccctctaaaggatgcaaaagtcgtaacacgg
tttccgtaggtgaacctgcggaaggatcattcACACATTTTCGGTCGC
GCGAACAAAAGGAGCCTCTCTCTCCGTTCACTCCTTTCTGCTGCA
ATTCAGTGGAATGTGGGGTGTGCAGATGGTCGTGTGTGACGGCTTTTT
GTCTTGTTGGCCGACTGGAATCCTTTTTGAACCTTTTTAATTCCTCCC
ACCTTTGAATCGGTTAAGAGTTTTCTTCCCACGACGAGTTTTCTTTGA
GAATAAAAGAGAATTGTTGCGCAGGTGGCTGCTTGCTCGTTGAGAGT
GGCTGGGCTGCATGCGCGCATGCGCGAAGAGAGAAAAAAGGACCCaaaac
tttcagcaatggatgtcttg 544-067D: 5'→ 3' (405 bp)
SEQ ID NO: 63
[SEQ ID NO: 25 is the ITS-1 region, displayed in Full Caps]
aagttgcgtaaatagagccctctaaaggatgcaaaagtcgtaacacgg
tttccgtaggtgaacctgcggaaggatcattcACACATTTTCGGTCGC

```
GCGAACAAAAGGAGCCTCTCTCTCCTCTGTTCACTCCTTTCTGCTGCA
ATTCAGTGGAATGTGGGGTGTGCAGATGGTCGTGTGTGACGGCTTTTT
GTCTTGTTGGCCGACTGGAATCCTTTTTGAACCTTTTTAATTCCTCCC
AACCTTTGAATCGGTTAAGAGTTTTCTTCCCACGACGAGTTTTCTTTG
AGAATAAAAGAGAATGTGTTGCGCAGGTGGCTGCTCGCTCGTTGAGAG
TGGCTGGGCTGCATGCGCGCATGCGAAGCGAGAAAAAAGGACCCaaaa
ctttcagcaatggatgtcttg
```

544-067E: 5'→ 3' (404 bp)
SEQ ID NO: 64
[SEQ ID NO: 26 is the ITS-1 region, displayed in Full Caps]

aagttgcgtaaatagagccctctaaaggatgcaaaagtcgtaacacgg
tttccgtaggtgaacctgcggaaggatcattcACACATTTTCGGTCGC
GCGAACAAAAGGAGCCTCTCTCTCCTCCGTTCACTCCTTTCTGCTGCA
ATTCAGTGGAATGTGGGGTGTGCAGATGGTCGTGTGTGACGGCTTTTT
GTCTTGTTGGCTGACTGGAATCCTTTTTGAACCTTTTTAATTCCTCCC
AACCTTTGAATCGGTTAAGAGTTTTCTTCCCACGACGAGTTTTCTTTG
GAGAATAAAAGAATTGTTGCGCAGGTGGCTGCTCGCTCGTTGAGAG
TGGCTGGGCTGCATGCGCGCATGCGAAGCGAGAAAAAAGGACCCaaaa
*tttcagcaatggatgtctt*

544-067F: 5'→ 3' (405 bp)
SEQ ID NO: 65
[SEQ ID NO: 27 is the ITS-1 region, displayed in Full Caps]

aagttgcgtaaatagagccctctaaaggatgcaaaagtcgtaacacgg
tttccgtaggtgaacctgcggaaggatcattcACACATTTTCGGTCGC
GCGAACAAAAGGAGCCTCTCTCTCCTCCGTTCACTCCTTTCTGCTGCA
ATTCAGTGGAATGTGGGGTGTGCAGATGGTCGTGTGTGACGGCTTTTT
GTCTTGTTGGCCGACTGGAATCCTTTTTGAACCTTTTTAATTCCTCCC
AACCTTTGAATCGGTTAAGAGTTTTCTTCCCACGACGAGTTTTCTTTG
AGAATAAAAGAGAATGTGTTGCGCAGGTGGCTGCTCGCTCGTTGAGAG
TGGCTGGGCTGCATACGCGCATGCGAAGCGAGAAAAAAGGACCCaaaa
*ctttcagcaatggatgtcttg*

544-067G: 5'→ 3' (407 bp)
SEQ ID NO: 66
[SEQ ID NO: 28 is the ITS-1 region, displayed in Full Caps]

aagttgcgtaaatagagccctctaaaggatgcaaaagtcgtaacacgg
tttccgtaggtgaacctgcggaaggatcattcACACATTTTCGGTCGC
GCGAACAAAAGGAGCCTCTCTCTCCTCCGTTCACTCCTTTCTGCTGCA
ATTCAGTGGAATGTGGGGTGTGCAGATGGTCGTGTGTGACGGCTTTTT
GTCTTGTTGGCCGACTGGAATCCTTTTTGAACCTTTTTAATTCCTCCC
AACCTTTGAATCGGTTAAGAGTTTTCTTCCCACGACGAGTTTTCTTTG
AGAATAAAAGAGATGTGTTGCGCAGGTGGCTGCTCGCTCGTTGAGAGT
GGCTGGGCTGCATGCTGCGCGCATGCGAAGAGAGAAAAAAGGACCCaa
aa*ctttcagcaatggatgtcttg*

544-064A: 5'→ 3' (405 bp)
SEQ ID NO: 67
[SEQ ID NO: 29 is the ITS-1 region, displayed in Full Caps]

aagttgcgtaaatagagccctctaaaggatgcaaaagtcgtaacacgg
tttccgtaggtgaacctgcggaaggatcattcACACATTTTCGGTCGC
GCGAACAAAAGGAGCCTCTCTCTCCTCCGTTCACTCCTTTCTGCTGCA
ATTCAGTGGAATGTGGGGTGTGCAGATGGTCGTGTGTGACGGCTTTTT
GTCTTGTTGGCCGACTGGAATCCTTTTTGAACCTTTTTAATTCCTCCC
AACCTTTGAATCGGTTAAGAGTTTTCTTCCCACGACGAGTTTTCTTTG
AGAATAAAAGAGAATGTGTTGCGCAGGTGGCTGCTCGCTCGTTGAGAG
TGGCTGGGCTGCATGCGCGCATGCGAAGAGAGAAAAAAGGACCCaaaa
*ctttcagcaatggatgtcttg*

544-065A: 5'→ 3' (405 bp)
SEQ ID NO: 68
[SEQ ID NO: 30 is the ITS-1 region, displayed in Full Caps]

aagttgcgtaaatagagccctctaaaggatgcaaaagtcgtaacacgg
tttccgtaggtgaacctgcggaaggatcattcACACATTTTCGGTCGC
GCGAACAAAAGGAGCCTCTCTCTCCTCCGTTCACTCCTTTCTGCTGCA
ATTCAGTGGAATGTGGGGTGTGCAGATGGTCGTGTGTGACGGCTTTTT
GTCTTGTTGGCCGACTGGAATCGTTTTTGAACCTTTTTAATTCCTCCC
AACCTTTGAATCGGTTAAGAGTTTTCTTCCCACGACGAGTTTTCTTTG
AGAATAAAAGAGAATGTGTTGCGCAGGTGGCTGCTCGCTCGTTGAGAG
TGGCTGGGCTGCATGCGCGCATGCGAAGAGAGAAAAAAGGACCCaaaa
*ctttcagcaatggatgtcttg*

UGA *E. meleagrimitis* 2 Isolates 544-066A: Large fragment 5'→ 3' (500 bp)
SEQ ID NO: 69
[SEQ ID NO: 31 is the ITS-1 region, displayed in Full Caps]

aagttgcgtaaatagagccctctaaaggatgcaaaagtcgtaacacgg
tttccgtaggtgaacctgcggaaggatcattcACACGTGATGCATGCA
GCAAGCTGGAAAGGTGCCTGTTTGTATGTGGGAAGTGCATTTATTATG
CACACCTGCATTCATGCGAGGTTACTGTCAATCCGGCGACTGCATGTA
TGGCTTCTTGGACCGCAATAACAACCTGTAAATCTCTTTTCTTCTCCA
CAACGGTTTTTCTTTTGTTTACGGTACTTTATTTGTGTACCACAACTA
TAAGTTGTTGGGGTTTTCAGCTGCTTCACTGTGCTACTGGATAGG
CTAGCTGCATTTGTTTTGCCGGTCGGGGTTGTTGTTCGGCAGGCACAG
CATGGCAGCAGGGCTGTCGGCAGTGGCAGGTGTTTGCAGTTGTGTACC
ATTTAATTCTGCTAAAGAGCAGAATGATTTGTTTACAAAAAAA*aaaac
tttcagcaatggatgtcttg*

544-067A: 5'→ 3' (502 bp)
SEQ ID NO: 70
[SEQ ID NO: 32 is the ITS-1 region, displayed in Full Caps]

aagttgcgtaaatagagccctctaaaggatgcaaaagtcgtaacacgg
tttccgtaggtgaacctgcggaaggatcattcACACGTGATGCATGCA
GCAAGCTGGAAAGGTGCCTGTTTGTATGTGGGAAGTGCATTTCTTATG
CACACCTGCATGCATGTGAGGTTACTGTCAAGCCGGCGACTGCATGTA
TGGCTTCTTGGACCGCAATAACAACCTGTAAATCTCTTTTCCTCT
CCACAACGGTTTTTCTTTTGTTTACGGTACTTTATTTGTGTACCACAA
CTATAAGTTCTTGGGGTTTTCAGCTGCTTCACTGTGCTACTGGATGAT
AGGCTAGCTGCATTTGTTTTGCCAGTCGGGGTTGCTGTTTGGCAGGCA
CAGCATGGCAGCAGGGGTGTTGGCAGTTGCAGTGTTTGCAGTTGTATA
CCATTTAATTCTGCTGAAGAGCAGAATGTTTTGTTTACAAAAAAA*aaa
actttcagcaatggatgtcttg*

544-067B: 5'→ 3' (503 bp)
SEQ ID NO: 71
[SEQ ID NO: 33 is the ITS-1 region, displayed in Full Caps]

aagttgcgtaaatagagccctctaaaggatgcaaaagtcgtaacacgg
tttccgtaggtgaacctgcggaaggatcattcACACGTGATGCATGCA
GCAAGCTGGACACACCTGCATGCATGAAGGTGCCTGTTTGTATGTGGG
AAGTGCATTTCTTATGTGAGGTTACTGTCAAGCCGGCGACTGCATGTA
TGGCTTCTTGGACCGCAATAACAACCTGTAAATCTCTTTTCCTCT
CCACAACGGTTTTTCTTTTGTTTACGGTACTTTATTTGTGTACCACAA
CTATAAGTTCTTGGGGTTTTCAGCTGCTTCACTGTGCTACTGGATGAT
AGGCTAGCTGCATTTGTTTTGCCAGTCGGGGTTGCTGTTTGGCAGGCA
CAGCATGGCAGCAGGGGTGTTGGCAGTTGCAGTGTTTGCAGTTGTATA
CCATTTAATTCTGCTGAAGAGCAGAATGTTTTGTTTACAAAAAAAAaa
aac*tttcagcaatggatgtcttg*

544-068A: 5'→ 3' (501 bp)
SEQ ID NO: 72
[SEQ ID NO: 34 is the ITS-1 region, displayed in Full Caps]

aagttgcgtaaatagagccctctaaaggatgcaaaagtcgtaacacgg
tttccgtaggtgaacctgcggaaggatcattcACACGTGATGCATGCA
GCAAGCTGGAAAGGTGCCTGTTTGTATGTGGGAAGTGCATTTCTTATG
CACACCTGCATGCATGTGGGGTTACTGTCAATCCGGCGACTGCATGTA
TGGCTTCTTGGACCGCAATAACAACCTGTAAATCTCTTTTCTTCT
CCACAACGTTTTTCCTTTGTTTACGGTGCTTTATTTGTGTACCACAA
CTATAAGTTGTTGGGGTTTTCAGCTGCTTCACTGTGCTACTGGATGAC
CGGCTAGCTGCATTTATTTTGCCAGTCGGGGTTGCTGTTCGGCAGGCA
CAGCATGGCAGCAGGGCTGTCGGCAGTGGCAGGTGTTTGCAGTTGTAT
ACCATTTAATTCTGCTGAAGAGCAGAATGTTTTGTTTACAAAAA*aaaa
ctttcagcaatggatgtcttg*

US-SPAH Isolates

*E. adenoeides*-SPAH-US (CAD) 5'→3' (417 bp)
SEQ ID NO: 75
[SEQ ID NO: 37 is the ITS-1 region, displayed in Full Caps]

aagttgcgtaaatagagccctctaaaggatgcaaaagtcgtaacacgg
tttccgtaggtgaacctgcggaaggatcattcACACGTGAAGCATGAA
KGCAGAGAAAGGATGCTTTTGATCAGATATATCTGCTTTGCTTGTAGG
TTTGCATTGGTTCTTGGTAACAAGTCGCCAAGCAGATTTGCATGCATG
CAGTTTTGTGATCATTATTTATAGCGCTCTTTCTTTGACTGCTGTTT
ATGCTTTTGTTATGGATTGGACACACATTACAAAATCTGTAAATCTTT
TTTCTTTTCTCACAACGAGTTTTCCTCTTTGAAATTTCTGGAAAGAAAG
```

-continued
AATATAGATTGCTGGCTGTGTATGTACCAGCAGAATGTGTAGAATGAA
AAAGTTGAAaaactttcagcaatggatgtcttg

*E. meleagrimitis* 1-SPAH-US (Eme) 5'→3' (403 bp)
SEQ ID NO: 76
[SEQ ID NO: 38 is the ITS-1 region, displayed in
Full Caps]
aagttgcgtaaatagagccctctaaaggatgcaaaagtcgtaacacgg
tttccgtaggtgaacctgcggaaggatcattcACACATTTTCGGTCGC
GCGAACAAAAGGAGCCTCTCTCTCCTCCGTTCACTCCTTTCTGCTGCA
ATTCAGTGGAATGTGGGGTGTGCAGATGGTCGTGTGTGACGGCTTTTT
GTCTTGTTGGCCGACTGGAATCCTTTTTGAACCTTTTTAATTCCTCCC
AACCTTTGAATCGGTTAAGAGTTTTCTTCCCACGACGAGTTTTCTTTG
AGAATAAAAGAGAATGTGTTGCGCAGGTGGCTGCTCGCTCGTTGAGAG
TGGCTGGGCTGCATGCGCGCATGCGAAGAGAGAAAAAAGGACCCA*aaa
ctttcagcaatggatgtct*

*E. gallopavonis*-SPAH-US (Ega) Large fragment
5'→3' (538 bp)
SEQ ID NO: 77
[SEQ ID NO: 39 is the ITS-1 region, displayed in
Full Caps]
taagttgcggtaaatagagccctctaaaggatgcaaaagtcgtaacac
ggtttccgtaggtgaacctgcggaaggatcattcACACGTAAAGCATG
AAAGCAGGGAAAGATACTTTTTGATCTTATCCGTTTGTTGATTGTTGT
GGGACAGTCAGCTTGCATGCGGGTTGGGTCACGAGTGTCTGCTGCTGT
TCAGGCTTATCCGGGTGGGACAAAGATTAACAACAACCTGTAAATCTG
TTTTTTTTCTCACAACGAGTTTTCTTTTTTTGCCGAAAAAGTCTTTTT
GCTGCTTCACTGTGTAGTGCGGTGTGGGTGTGGCGGCAGGTGTTGTGA
TCTCCATAACTCCCCTCCCATGCATCATCATGACCAGTGTTGGTACT
GGTTTGTTGGTGCTGATAGGGGAACGTTATGTAGAGGACCCATAGCCG
TTACACAACGTTTCCGGCCTCAGTGTATTGCAGGGACTTTATTCTGTA
TATACTAACAGAATGTATATATGAAGCCAAA*aaactttcagcaatgg
aatgtcttga*

*E. gallopavonis*-SPAH-US (Ega): Small fragment
5'→3' (392 bp)
SEQ ID NO: 78
[SEQ ID NO: 40 is the ITS-1 region, displayed in
Full Caps]
aagttgcgtaaatagagccctctaaaggatgcaaaagtcgtaacacgg
tttccgtaggtgaacctgcggaaggatcattcACACGTATAAAGCATG
AAAGCAGGAAGAGACATATTTCTTTTATTTGATCTCCTCCTATATCCT
TCTTGAGAGATCTGCGTTTACGCGGCTTGATCAAGTTTGGTGGTGGTT
GGTCAATAGAAGAGGTGTCTTTTTGACTGGTCTTTTCAGGCTTATTAT
GGGATAATATTCAACCACAACCTGTAAATCTCTTTTTCCTCTCTCACA
ACAACGAGTTTTCTGTAGATTGCAATTGATGCAAGTGTATTCTGTACG
CTACAGAATATAAAGGTACAAAAAGAAAAAA*aaactttcagcaatg
gatgtctt*

UR Reference Isolates

*E. meleagrimitis* 2 5'→3' (475 bp)
SEQ ID NO: 73
[SEQ ID NO: 35 is the ITS-1 region, displayed
in Full Caps]
gcatgcagtcgtacacggtttccgtaggtgaacctgcggaaggatcat
tcACACGTGATGCATGCAGCAAGCTGGAAAGGTGCCTGTTTGTATGTG
GGAAGTGCATTTCTTATGCACACCTGCATTCATGCGAGGTTACTGTCA
ATCCGGCGACTGCATGTATGGCTTCTTGGACCGCAATAACAACAACCT
GTAAATCTCTTTTCCTCTCCACAACGGTTTTTCTTTTGTTTACGGTAC
TTTATTTGTGTACCACAACTATAAGTTGTTGGGGTTTTCAGCTGCTTC
ACTGTGCTACTGGATGATAGGCTAGCTGCATTTGTTTTGCCGGTCGGG
GTTGTTGTTCGGCAGGCACAGCATGCAGCAGGGCTGTCGGCAGCCGC
AGGTGTTTGCAGTTGTATACCATTTAATTCTGCTAAAAAGCAAAATGT
TTTGTTTACAAAAAAAAAATTTTTCAACGGTGGTTTTGAGGAA

*E. gallopavonis*-large fragment 5'→3' (506 bp)
SEQ ID NO: 74
[SEQ ID NO: 36 is the ITS-1 region, displayed in
Full Caps]
gtcgtcaagtcgtacacggtttccgtaggtgaacctgcggaaggatca
ttcACACGTAAAGCATGAAAGCAGGGAAAGATACTTTTTGATCTTATC
CGTTTGTTGATTGTTGTGGGACAGTCAGCTTGCATGCGGGTTGGGTCA
CGAGTGTCTGCTGCTGTTCAGGCTTATCCGGGTGGGACAAAGATTAAC
AACAACCTGTAAATCTGTTTTTTTCTCACAACGAGTTTTCTTTTTTTT
GCCGAAAAGTCTTTTTGCTGCTTCACTGTGTAGTGCGGTGTGGGTGT
GGCGGCAGGTGTTGTGATCTCCATAACTCCCCTCCCATGCATCATCAT
GACCAGTGTTGGGTACTGGTTTGTTGGTGCTGATAGGGGAACGTTATG
TAGAGGACCCATAGCCGTTACACAACGTTTCCGGCCTCAGTGTATTGC -continued
AGGGACTTTATTCTGTATATACTAACAGAATGTATATATGAAGCCAAA
A*aaactttcagcaatggatgtcttga*

*E. gallopavonis*-small fragment 5'→3' (355 bp)
SEQ ID NO: 79
[SEQ ID NO: 41 is the ITS-1 region, displayed in
Full Caps]
**gtaatcagtcgtacacggtttccgtaggtgaacctgcggaaggatcat
tc**ACACGTATAAAGCATGAAAGCAGGAAGAGACATATTTCTTTTATTT
GATCTCCTCCTATATCCTTCTTGAGAGATCTGCGTTTACGCGGCTTGA
TCAAGTTTGGTGGTGGTTGGTCAATAGAAGAGGTGTCTTTTTGACTGG
TCTTTTCAGGCTTATTATGGGATAATATTCAACCGCAACCTGTAAATC
TCTTTTTCCTCTCTCACAACAACGAGTTTTCTGTAGATTGCAATTGAT
GCAAGTGTATTCTGTACGCTACAGAATATAAAGGTACAAAAAGAAAAA
A*aaaactttcagcaagga*

*E. dispersa* 5'→3' (373 bp)
SEQ ID NO: 80
[SEQ ID NO: 42 is the ITS-1 region, displayed in
Full Caps]
**tagatcagtcgtacacggtttccgtaggtgaacctgcggaaggatcat
tc**ACACATTCTGTCCAACAGGAGCTGGTATTCATTCATTTCTGTGTGA
AATGGCACAGATGGGTGTTGCAAGCTTCCTGTCTTGGGCGGCTGGGTA
TTGAACCTTTTTATCCCTCCCACAACCTTTGAATCGGTTTGTTGAGTT
TTCTTTCCACGACGAGTTTTCTTAAAATTTAAAAGAATGAAAGTTGCG
CCCTTGCTGGTCACTCATTGAGAGCCGCATTTGTAACTGCTCTCGAGA
GCAGTGGAAGCGGGGCTTTTTAAGTGAGTGGCTGCATGCGCGCATGCG
TAATATTTATCAGCTCTTA*aaactttcagcatggaaa*

UK-SPAH Isolates

*E. meleagrimitis* 2-SPAH-UK 5'→3' (268 bp)
SEQ ID NO: 81
[SEQ ID NO: 43 is the ITS-1 region, displayed in
Full Caps]
cggtttccgtaggtgaacctgcggaaggatcattcACACGTGATGCAT
GCAGCAAGCTGGAAAGGTGCCTGTTTGTATGTGGGAAGTGCATTTCTT
ATGCACACCTGCATGCATGTGAGGTTACTGTCAATCCGGCGACTGCAT
GTATGGCTTCTTGGACCGCAATAACAACAACCTGTAAATCTCTTTTCC
TCTCCACAACGGTTTTTCTTTTGTTTACGGTACTTTATTTGTGTACCA
CAACTATAAGTTGTTGGGGTTTTCAGCT

*E. meleagrimitis*-2 Consensus Sequence

Consensus sequence for *E. meleagrimitis* 2 5'→3'
(409 bp)
SEQ ID NO: 44
ACACGTGANGCATGCANNNAGCTGGAAANNTNGCCTGTTTGTATGTGG
GAAGTGCATTTNTTATGCACACCTGCATNCATGNGNGGTTACTGTCAA
NCCGGCGANCTGCATGTATGGCTTCTTGGACCGCAATAACANNNACCT
GTAAATCNCTTTTNNTCTCCACAACGGTTTTTCNTTTGTTTACGGTNC
TTTATTTGTGTACCACAACTATAAGTTNTTGGGGTTTTCNGCTGCTTC
ACTGTGCTACTGGNTGANNNNNNGGCTAGCTGCATTTNTTTTGCCNG
TCGGGGTTGNTGTFNGGCAGGCNCAGCATGGCAGCAGGGNTGTNGGCA
GTNGCAGNNGTTTGCAGTTGNNTACNATTTANTTCTGCTNAANAGCAN
NATGNTTTGTTTACAAAAAAAANNNN (5.8S end)
Where "N" can be any nucleotide or no nucleotide It is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

SEQUENCE LISTING

<160> NUMBER OF SEQ ID NOS: 81

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
aagttgcgta aatagagccc                                                     20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
caagacatcc attgctgaaa                                                     20

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
ctctcctccg ttcactcctt tctg                                                24

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
agccacctgc gcaacacatt ct                                                  22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
gcttgtaggt ttgcattggt tc                                                  22

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
ctcgttgtga gaaagaaaa aagat                                                25

<210> SEQ ID NO 7
<211> LENGTH: 21
<212> TYPE: DNA

<213> ORGANISM: Artificial Sequence
<220> FEATURE:
<223> OTHER INFORMATION: Primer

<400> SEQUENCE: 7
tccgtttgtt gattgttgtg g                                     21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tcccctatca gcaccaacaa a                                     21

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
caggagctgg tattcattca tttct                                 25

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
agggcgcaac tttcattctt t                                     21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctggaaaggt gcctgtttgt                                       20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
agcacagtga agcagctgaa                                       20

<210> SEQ ID NO 13
<211> LENGTH: 429
<212> TYPE: DNA
<213> ORGANISM: Eimeria gallopavonis

<400> SEQUENCE: 13
acacgtaaag catgaaagca gggaaagata cttttttgatc ttatccgttt gttgattgtt      60
gtgggacagt cagcttgcat gagggttggg tcacgagtgt ctgctgctgt tcaggcttat     120

-continued

```
ccgggtggga caaagattaa caacaacctg taaatctgtt ttttctcac aacgagtttt      180 cttttttttg ccgaaaaagt cttttgctg cttcactgtg tagtgcggtg tgggtgtggc      240
ggcaggtgtt gtgatctcca taactccct cccatgcatc atcatgacca gtgttgggta      300
ctggtttgtt ggtgctgata ggggaacgtt atgtagagga cccatagccg ttacacaacg      360
tttccggcct cagtgtattg cagggacttt attctgtata tactaacaga atgtatatat      420
gaagccaaa                                                              429
```

<210> SEQ ID NO 14
<211> LENGTH: 287
<212> TYPE: DNA
<213> ORGANISM: Eimeria gallopavonis

<400> SEQUENCE: 14

```
acacgtataa agcatgaaag caggaagaga catatttctt ttatttgatc tcctcctata      60
tccttcttga gagatctgcg tttacgcggc ttgatcaagt ttggtggtgg ttggtcaata     120
gaagaggtgt cttttgact ggtctttca ggcttattat gggataatat tcaaccgcaa      180
cctgtaaatc tctttttcct ctctcacaac aacgagtttt ctgtagattg caattgatgc     240
aagtgtattc tgtacgctac agaatataaa ggtacaaaaa gaaaaaa                   287
```

<210> SEQ ID NO 15
<211> LENGTH: 429
<212> TYPE: DNA
<213> ORGANISM: Eimeria gallopavonis

<400> SEQUENCE: 15

```
acacgtaaag catgaaagca gggaaagata cttttgatc ttatccgttt gttgattgtt      60
gtgggacagt cagcttgcat gcgggttggg tcacgagtgt ctgctgctgt tcaggcttat     120
ccgggtggga caaagattaa caacaacctg taaatctgtt ttttctcac aacgagtttt      180 cttttttttg ccgaaaaagt cttttgctg cttcactgtg tagtgcggtg tgggtgtggc      240
ggcaggtgtt gtgatctcca taactccct cccatgcatc atcatgacca gtgttgggta      300
ctggtttgtt ggtgctgata ggggaacgtt atgtagagga cccatagccg ttacacaacg      360
tttccggcct cagtgtattg cagggacttt attctgtata tactaacaga atgtatatat      420
gaagccaaa                                                              429
```

<210> SEQ ID NO 16
<211> LENGTH: 287
<212> TYPE: DNA
<213> ORGANISM: Eimeria gallopavonis

<400> SEQUENCE: 16

```
acacgtataa agcatgaaag caggaagaga catatttctt ttatttgatc tcctcctata      60
tccttcttga gagatctgcg tttacgcggc ttgatcaagt ttggtggtgg ttggtcaata     120
gaagaggtgt cttttgact ggtctttca ggcttattat gggataatat tcaaccgcaa      180
cctgtaaatc tctttttcct ctctcacaac aacgagtttt ctgtagattg caattgatgc     240
aagtgtattc tgtacgctac agaatataaa ggtgcaaaaa gaaaaaa                   287
```

<210> SEQ ID NO 17
<211> LENGTH: 429
<212> TYPE: DNA
<213> ORGANISM: Eimeria gallopavonis

<400> SEQUENCE: 17

-continued

```
acacgtaaag catgaaagca gggaaagata cttttttgatc ttatccgttt gttgattgtt      60
gtgggacagt cagcttgcat gcgggttggg tcacgaatgt ctgctgctgt tcaggcttat     120
ccgggtggga caaagattaa caacaacctg taaatctgtt tttttctcac aacgagtttt     180
cttttttttg ccgaaaaagt cttttgctg cttcactgtg tagtgcggtg tgggtgtggc     240
ggcaggtgtt gtgatctcca taactcccct cccatgcatc atcatgacca gtgttgggta     300
ctggtttgtt ggtgctgata ggaacgtt atgtagagga cccatagccg ttacacaacg     360
tttccggcct cagtgtattg cagggacttt attctgtata tactaacaga atgtatatat     420
gaagccaaa                                                              429
```

<210> SEQ ID NO 18
<211> LENGTH: 312
<212> TYPE: DNA
<213> ORGANISM: Eimeria adenoeides

<400> SEQUENCE: 18

```
acacgtgaag catgaaggca gagaaaggat gcttttgatc agatatatct gctttgcttg      60
taggtttgca ttggttcttg gtaacaagtc gccaagcaga tttgcatgca tgcagttttg     120
tgatcattat ttatagcgtc actttctttg actgctgttt atgcttttgt tatggattgg     180
acacacatta caaatctgt aaatcttttt tcttttctca caacgagttt tctctttgaa     240
atttctggaa agaaagaata tagattgctg gctgtgtatg taccagcaga atgtgtagaa     300
tgaaaaagtt ga                                                          312
```

<210> SEQ ID NO 19
<211> LENGTH: 312
<212> TYPE: DNA
<213> ORGANISM: Eimeria adenoeides

<400> SEQUENCE: 19

```
acacgtgaag catgaaggca gagaaaggat gcttttgatc agatatatct gctttgcttg      60
taggtttgca ttggttcttg gtaacaagtc gccaagcaga tttgcatgca tgcagttttg     120
tgatcattat ttatagcgtc actttctttg gctgctgttt atgcttttgt tatggattgg     180
acacacatta caaatctgt aaatcttttt tcttttctca caacgagttt tctctttgaa     240
atttctggaa agaaagaata tagattgctg gctgtgtatg taccagcaga atgtgtagaa     300
tgaaaaagtt ga                                                          312
```

<210> SEQ ID NO 20
<211> LENGTH: 312
<212> TYPE: DNA
<213> ORGANISM: Eimeria adenoeides

<400> SEQUENCE: 20

```
acacgtgaag catgaatgca gagaaaggat gcttttgatc agatatatct gctttgcttg      60
taggtttgca ttggttcttg gtaacaagtc gccaagcaga tttgcatgca tgcagtttag     120
tgatcattat ttatagcgtc tctttctttg actgctgttt atgcttttgt tatggattgg     180
acacacatta caaatctgt aaatcttttt tcttttctca caacgagttt tctctttgaa     240
atttctggaa agaaagaata tagattgctg gctgtgtatg taccagcaga atgtgtagaa     300
tgaaaaagtt ga                                                          312
```

<210> SEQ ID NO 21
<211> LENGTH: 312
<212> TYPE: DNA

<213> ORGANISM: Eimeria adenoeides

<400> SEQUENCE: 21

| | | |
|---|---|---|
| acacgtgaag catgaatgca gagaaaggat gcttttgatc agatatatct gctttgcttg | 60 |
| taggtttgca ttggttcttg gtaacaagtc gccaagcaga tttgcatgca tgcagttttg | 120 |
| tgatcattat ttatagcgtc tctttctttg actgctgttt atgcttttgt tatgggttgg | 180 |
| acacacatta caaaatctgt aaatctttt tcttttctca caacgagttt tctctttgaa | 240 |
| atttctggaa agaaagaata tagattgctg gctgtgtatg taccagcaga atgtgtagaa | 300 |
| tgaaaaagtt ga | 312 |

<210> SEQ ID NO 22
<211> LENGTH: 304
<212> TYPE: DNA
<213> ORGANISM: Eimeria dispersa

<400> SEQUENCE: 22

| | |
|---|---|
| acacattctg tccaacagga gctggtattc attcatttct gtgtgaaatg gcatagatgg | 60 |
| gtgttgcaag cttcctgtct tgggcggctg agtattgaac cttttttatcc ctcccacaac | 120 |
| ctttgaatcg gtttgttgag ttttctttcc acgacgagtt ttcttaatat ttaaaagaat | 180 |
| gaaagttgcg cccttgctgg ccactcattg agagccgcat ttgtaactgc tctcgtgagc | 240 |
| agtggaagcg gggctttttc agtgagtggc tgcatgcgcg catgcgtaat atttatcagc | 300 |
| tctt | 304 |

<210> SEQ ID NO 23
<211> LENGTH: 304
<212> TYPE: DNA
<213> ORGANISM: Eimeria dispersa

<400> SEQUENCE: 23

| | |
|---|---|
| acacattctg tccaacagga gctggtattc attcatttct gtgtgaaatg gcacagatgg | 60 |
| gtgttgcaag cttcctgtct tgggcggctg agtattgaac cttttttatcc ctcccacaac | 120 |
| ctttgaatcg gtttgttgag ttttctttcc acgacgagtt ttcttaaaat ttaaaagaat | 180 |
| gaaagttgcg cccttgctgg tcactcattg agagccgcat ttgtaactgc tctcgagagc | 240 |
| agaggaagcg gggcttttta ggtgagtggc tgcatgcgcg catgcgtaat atttatcagc | 300 |
| tctt | 304 |

<210> SEQ ID NO 24
<211> LENGTH: 300
<212> TYPE: DNA
<213> ORGANISM: Eimeria meleagrimitis 1

<400> SEQUENCE: 24

| | |
|---|---|
| acacattttc ggtcgcgcga acaaaaggag cctctctctc ctccgttcac tcctttctgc | 60 |
| tgcaattcag tggaatgtgg ggtgtgcaga tggtcgtgtg tgacggcttt ttgtcttgtt | 120 |
| ggccgactgg aatccttttt gaaccttttt aattcctccc aacctttgaa tcggttaaga | 180 |
| gttttcttcc cacgacgagt tttctttgag aataaaagag aatgtgttgc gcaggtggct | 240 |
| gcttgctcgt tgagagtggc tgggctgcat gcgcgcatgc gaagagagaa aaaaggaccc | 300 |

<210> SEQ ID NO 25
<211> LENGTH: 300
<212> TYPE: DNA
<213> ORGANISM: Eimeria meleagrimitis 1

-continued

<400> SEQUENCE: 25

```
acacattttc ggtcgcgcga acaaaaggag cctctctctc ctctgttcac tcctttctgc    60
tgcaattcag tggaatgtgg ggtgtgcaga tggtcgtgtg tgacggcttt ttgtcttgtt   120
ggccgactgg aatccttttt gaaccttttt aattcctccc aacctttgaa tcggttaaga   180
gttttcttcc cacgacgagt tttctttgag aataaaagag aatgtgttgc gcaggtggct   240
gctcgctcgt tgagagtggc tgggctgcat gcgcgcatgc gaagagagaa aaaaggaccc   300
```

<210> SEQ ID NO 26
<211> LENGTH: 300
<212> TYPE: DNA
<213> ORGANISM: Eimeria meleagrimitis 1

<400> SEQUENCE: 26

```
acacattttc ggtcgcgcga acaaaaggag cctctctctc ctccgttcac tcctttctgc    60
tgcaattcag tggaatgtgg ggtgtgcaga tggtcgtgtg tgacggcttt ttgtcttgtt   120
ggctgactgg aatccttttt gaaccttttt aattcctccc aacctttgaa tcggttaaga   180
gttttcttcc cacgacgagt tttctttgag aataaaagag aatgtgttgc gcaggtggct   240
gctcgctcgt tgagagtggc tgggctgcat gcgcgcatgc gaagcgagaa aaaaggaccc   300
```

<210> SEQ ID NO 27
<211> LENGTH: 300
<212> TYPE: DNA
<213> ORGANISM: Eimeria meleagrimitis 1

<400> SEQUENCE: 27

```
acacattttc ggtcgcgcga acaaaaggag cctctctctc ctccgttcac tcctttctgc    60
tgcaattcag tggaatgtgg ggtgtgcaga tggtcgtgtg tgacggcttt ttgtcttgtt   120
ggccgactgg aatccttttt gaaccttttt aattcctccc aacctttgaa tcggttaaga   180
gttttcttcc cacgacgagt tttctttgag aataaaagag aatgtgttgc gcaggtggct   240
gctcgctcgt tgagagtggc tgggctgcat acgcgcatgc gaagcgagaa aaaaggaccc   300
```

<210> SEQ ID NO 28
<211> LENGTH: 302
<212> TYPE: DNA
<213> ORGANISM: Eimeria meleagrimitis 1

<400> SEQUENCE: 28

```
acacattttc ggtcgcgcga acaaaaggag cctctctctc ctccgttcac tcctttctgc    60
tgcaattcag tggaatgtgg ggtgtgcaga tggtcgtgtg tgacggcttt ttgtcttgtt   120
ggccgactgg aatccttttt gaaccttttt aattcctccc aacctttgaa tcggttaaga   180
gttttcttcc cacgacgagt tttctttgag aataaaagag atgtgttgcg caggtggctg   240
ctcgctcgtt gagagtggct gggctgcatg ctgcgcgcat gcgaagagag aaaaaaggac   300
cc                                                                 302
```

<210> SEQ ID NO 29
<211> LENGTH: 300
<212> TYPE: DNA
<213> ORGANISM: Eimeria meleagrimitis 1

<400> SEQUENCE: 29

```
acacattttc ggtcgcgcga acaaaaggag cctctctctc ctccgttcac tcctttctgc    60
tgcaattcag tggaatgtgg ggtgtgcaga tggtcgtgtg tgacggcttt ttgtcttgtt   120
```

```
ggccgactgg aatccttttt gaaccttttt aattcctccc aacctttgaa tcggttaaga      180
gttttcttcc cacgacgagt tttctttgag aataaaagag aatgtgttgc gcaggtggct      240
gctcgctcgt tgagagtggc tgggctgcat gcgcgcatgc gaagagagaa aaaggaccc      300

<210> SEQ ID NO 30
<211> LENGTH: 300
<212> TYPE: DNA
<213> ORGANISM: Eimeria meleagrimitis 1

<400> SEQUENCE: 30
acacattttc ggtcgcgcga acaaaaggag cctctctctc ctccgttcac tccttctgc       60 tgcaattcag tggaatgtgg ggtgtgcaga tggtcgtgtg tgacggcttt ttgtcttgtt     120
ggccgactgg aatcgttttt gaaccttttt aattcctccc aacctttgaa tcggttaaga    180
gttttcttcc cacgacgagt tttctttgag aataaaagag aatgtgttgc gcaggtggct    240
gctcgctcgt tgagagtggc tgggctgcat gcgcgcatgc gaagagagaa aaaggaccc    300

<210> SEQ ID NO 31
<211> LENGTH: 395
<212> TYPE: DNA
<213> ORGANISM: Eimeria meleagrimitis 2

<400> SEQUENCE: 31
acacgtgatg catgcagcaa gctggaaagg tgcctgtttg tatgtgggaa gtgcatttat       60
tatgcacacc tgcattcatg cgaggttact gtcaatccgg cgactgcatg tatggcttct     120
tggaccgcaa taacaacctg taaatctctt ttcttctcca caacggtttt tcttttgttt     180
acggtacttt atttgtgtac cacaactata agttgtgggg ttttcagct gcttcactgt      240 gctactggat gataggctag ctgcatttgt tttgccggtc ggggttgttg ttcggcaggc    300
acagcatggc agcagggctg tcggcagtgg caggtgtttg cagttgtgta ccatttaatt     360
ctgctaaaga gcagaatgat tgtttacaa aaaaa                                 395

<210> SEQ ID NO 32
<211> LENGTH: 397
<212> TYPE: DNA
<213> ORGANISM: Eimeria meleagrimitis 2

<400> SEQUENCE: 32
acacgtgatg catgcagcaa gctggaaagg tgcctgtttg tatgtgggaa gtgcatttct       60
tatgcacacc tgcatgcatg tgaggttact gtcaagccgg cgactgcatg tatggcttct     120
tggaccgcaa taacaacaac ctgtaaatct cttttcctct ccacaacggt ttttcttttg     180
tttacggtac tttatttgtg taccacaact ataagttctt ggggttttca gctgcttcac    240
tgtgctactg gatgataggc tagctgcatt tgttttgcca gtcggggttg ctgtttggca    300
ggcacagcat ggcagcaggg gtgttggcag ttgcagtgtt gcagttgta taccatttaa      360 ttctgctgaa gagcagaatg ttttgtttac aaaaaaa                             397

<210> SEQ ID NO 33
<211> LENGTH: 398
<212> TYPE: DNA
<213> ORGANISM: Eimeria meleagrimitis 2

<400> SEQUENCE: 33
acacgtgatg catgcagcaa gctggaaagg tgcctgtttg tatgtgggaa gtgcatttct       60
tatgcacacc tgcatgcatg tgaggttact gtcaagccgg cgactgcatg tatggcttct    120
```

```
tggaccgcaa taacaacaac ctgtaaatct cttttcctct ccacaacggt ttttcttttg      180
tttacggtac tttatttgtg taccacaact ataagttctt ggggttttca gctgcttcac      240
tgtgctactg gatgataggc tagctgcatt tgttttgcca gtcggggttg ctgtttggca      300
ggcacagcat ggcagcaggg gtgttggcag ttgcagtgtt tgcagttgta taccatttaa      360
ttctgctgaa gagcagaatg ttttgtttac aaaaaaaa                              398

<210> SEQ ID NO 34
<211> LENGTH: 396
<212> TYPE: DNA
<213> ORGANISM: Eimeria meleagrimitis 2

<400> SEQUENCE: 34
acacgtgatg catgcagcaa gctggaaagg tgcctgtttg tatgtgggaa gtgcatttct       60
tatgcacacc tgcatgcatg tggggttact gtcaatccgg cgactgcatg tatggcttct      120
tggaccgcaa taacaacaac ctgtaaatct cttttcttct ccacaacggt ttttcctttg      180
tttacggtgc tttatttgtg taccacaact ataagttgtt ggggttttca gctgcttcac      240
tgtgctactg gatgaccggc tagctgcatt tattttgcca gtcggggttg ctgttcggca      300
ggcacagcat ggcagcaggg ctgtcggcag tggcaggtgt ttgcagttgt ataccattta      360
attctgctga agagcagaat gttttgttta caaaaa                                396

<210> SEQ ID NO 35
<211> LENGTH: 425
<212> TYPE: DNA
<213> ORGANISM: Eimeria meleagrimitis 2

<400> SEQUENCE: 35
acacgtgatg catgcagcaa gctggaaagg tgcctgtttg tatgtgggaa gtgcatttct       60
tatgcacacc tgcattcatg cgaggttact gtcaatccgg cgactgcatg tatggcttct      120
tggaccgcaa taacaacaac ctgtaaatct cttttcctct ccacaacggt ttttcttttg      180
tttacggtac tttatttgtg taccacaact ataagttgtt ggggttttca gctgcttcac      240
tgtgctactg gatgataggc tagctgcatt tgttttgccg gtcggggttg ttgttcggca      300
ggcacagcat ggcagcaggg ctgtcggcag tggcaggtgt ttgcagttgt ataccattta      360
attctgctaa aaagcaaaat gttttgttta caaaaaaaaa attttcaac ggtggttttg      420 aggaa                                                                   425

<210> SEQ ID NO 36
<211> LENGTH: 430
<212> TYPE: DNA
<213> ORGANISM: Eimeria gallopavonis

<400> SEQUENCE: 36
acacgtaaag catgaaagca gggaaagata cttttgatc ttatccgttt gttgattgtt       60
gtgggacagt cagcttgcat gcgggttggg tcacgagtgt ctgctgctgt tcaggcttat      120
ccgggtggga caaagattaa caacaacctg taaatctgtt ttttctcac aacgagtttt      180 cttttttttg ccgaaaaagt cttttgctg cttcactgtg tagtgcggtg tgggtgtggc      240
ggcaggtgtt gtgatctcca taactcccct cccatgcatc atcatgacca gtgttgggta      300 ctggttttgtt ggtgctgata ggggaacgtt atgtagagga cccatagccg ttacacaacg      360
tttccggcct cagtgtattg cagggacttt attctgtata tactaacaga atgtatatat      420
gaagccaaaa                                                              430
```

<210> SEQ ID NO 37
<211> LENGTH: 313
<212> TYPE: DNA
<213> ORGANISM: Eimeria adenoeides

<400> SEQUENCE: 37

```
acacgtgaag catgaakgca gagaaaggat gcttttgatc agatatatct gctttgcttg    60 taggttttgca ttggttcttg gtaacaagtc gccaagcaga tttgcatgca tgcagttttg   120
tgatcattat ttatagcgtc tctttctttg actgctgttt atgcttttgt tatggattgg   180
acacacatta caaatctgt aaatctttttt tcttttctca caacgagttt tctcttttgaa   240 atttctggaa agaaagaata tagattgctg gctgtgtatg taccagcaga atgtgtagaa   300
tgaaaaagtt gaa                                                      313
```

<210> SEQ ID NO 38
<211> LENGTH: 301
<212> TYPE: DNA
<213> ORGANISM: Eimeria meleagrimitis 1

<400> SEQUENCE: 38

```
acacattttc ggtcgcgcga acaaaaggag cctctctctc ctccgttcac tcctttctgc    60
tgcaattcag tggaatgtgg ggtgtgcaga tggtcgtgtg tgacggcttt ttgtcttgtt   120
ggccgactgg aatcctttttt gaacctttttt aattcctccc aacctttgaa tcggttaaga   180
gttttcttcc cacgacgagt tttctttgag aataaaagag aatgtgttgc gcaggtggct   240
gctcgctcgt tgagagtggc tgggctgcat gcgcgcatgc gaagagagaa aaaaggaccc   300
a                                                                    301
```

<210> SEQ ID NO 39
<211> LENGTH: 430
<212> TYPE: DNA
<213> ORGANISM: Eimeria gallopavonis

<400> SEQUENCE: 39

```
acacgtaaag catgaaagca gggaaagata cttttttgatc ttatccgttt gttgattgtt    60
gtgggacagt cagcttgcat gcgggttggg tcacgagtgt ctgctgctgt tcaggcttat   120
ccgggtggga caaagattaa caacaacctg taaatctgtt tttttctcac aacgagtttt   180
cttttttttg ccgaaaaagt ccttttttgctg cttcactgtg tagtgcggtg tgggtgtggc   240
ggcaggtgtt tgatctcca taactcccct cccatgcatc atcatgacca gtgttgggta   300
ctggtttgtt ggtgctgata ggggaacgtt atgtagagga cccatagccg ttacacaacg   360
tttccggcct cagtgtattg cagggacttt attctgtata tactaacaga atgtatatat   420
gaagccaaaa                                                          430
```

<210> SEQ ID NO 40
<211> LENGTH: 288
<212> TYPE: DNA
<213> ORGANISM: Eimeria gallopavonis

<400> SEQUENCE: 40

```
acacgtataa agcatgaaag caggaagaga catatttctt ttatttgatc tcctcctata    60
tccttcttga gagatctgcg tttacgcggc ttgatcaagt ttggtggtgg ttggtcaata   120
gaagaggtgt ctttttgact ggtcttttca ggcttattat gggataatat tcaaccacaa   180
cctgtaaatc tcttttttcct ctctcacaac aacgagtttt ctgtagattg caattgatgc   240
```
aagtgtattc tgtacgctac agaatataaa ggtacaaaaa gaaaaaaa 288

<210> SEQ ID NO 41
<211> LENGTH: 287
<212> TYPE: DNA
<213> ORGANISM: Eimeria gallopavonis

<400> SEQUENCE: 41
acacgtataa agcatgaaag caggaagaga catatttctt ttatttgatc tcctcctata 60
tccttcttga gagatctgcg tttacgcggc ttgatcaagt ttggtggtgg ttggtcaata 120
gaagaggtgt ctttttgact ggtcttttca ggcttattat gggataatat tcaaccgcaa 180
cctgtaaatc tctttttcct ctctcacaac aacgagtttt ctgtagattg caattgatgc 240
aagtgtattc tgtacgctac agaatataaa ggtacaaaaa gaaaaaa 287

<210> SEQ ID NO 42
<211> LENGTH: 305
<212> TYPE: DNA
<213> ORGANISM: Eimeria dispersa

<400> SEQUENCE: 42
acacattctg tccaacagga gctggtattc attcatttct gtgtgaaatg gcacagatgg 60
gtgttgcaag cttcctgtct tgggcggctg ggtattgaac ctttttatcc ctcccacaac 120
ctttgaatcg gtttgttgag ttttctttcc acgacgagtt ttcttaaaat ttaaaagaat 180
gaaagttgcg cccttgctgg tcactcattg agagccgcat ttgtaactgc tctcgagagc 240
agtggaagcg gggcttttta agtgagtggc tgcatgcgcg catgcgtaat atttatcagc 300
tctta 305

<210> SEQ ID NO 43
<211> LENGTH: 233
<212> TYPE: DNA
<213> ORGANISM: Eimeria meleagrimitis 2

<400> SEQUENCE: 43
acacgtgatg catgcagcaa gctggaaagg tgcctgtttg tatgtgggaa gtgcatttct 60
tatgcacacc tgcatgcatg tgaggttact gtcaatccgg cgactgcatg tatggcttct 120
tggaccgcaa taacaacaac ctgtaaatct cttttcctct ccacaacggt ttttcttttg 180
tttacggtac tttatttgtg taccacaact ataagttgtt ggggttttca gct 233

<210> SEQ ID NO 44
<211> LENGTH: 409
<212> TYPE: DNA
<213> ORGANISM: Eimeria meleagrimitis 2
<220> FEATURE:
<221> NAME/KEY: misc_feature
<222> LOCATION: (1)..(409)
<223> OTHER INFORMATION: “n” can be any nucleotide or missing

<400> SEQUENCE: 44
acacgtgang catgcannna gctggaaann tngcctgttt gtatgtggga agtgcatttn 60
ttatgcacac ctgcatncat gngnggttac tgtcaanccg gcganctgca tgtatggctt 120
cttggaccgc aataacannn acctgtaaat cncttttnnt ctccacaacg gtttttcntt 180
tgtttacggt nctttatttg tgtaccacaa ctataagttn ttggggtttt cngctgcttc 240
actgtgctac tggntgannn nnnggctagc tgcatttntt ttgccngtcg gggttgntgt 300
tnggcaggcn cagcatggca gcagggntgt nggcagtngc agnngtttgc agttgnntac 360

```
natttanttc tgctnaanag cannatgntt tgtttacaaa aaaaannnn                    409
```

```
<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
agcatgaaag cagggaaaga                                                    20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
tgtaacggct atgggtcctc                                                    20

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
agcgtctctt tctttgactg c                                                  21

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
tggtacatac acagccagca a                                                  21

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
gtgtgaaatg gcacagatgg                                                    20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
tacaaatgcg gctctcaatg                                                    20

<210> SEQ ID NO 51
<211> LENGTH: 534
<212> TYPE: DNA
<213> ORGANISM: Eimeria gallopavonis
```

<400> SEQUENCE: 51

```
aagttgcgta aatagagccc tctaaaggat gcaaaagtcg taacacggtt tccgtaggtg      60
aacctgcgga aggatcattc acacgtaaag catgaaagca gggaaagata cttttttgatc    120
ttatccgttt gttgattgtt gtgggacagt cagcttgcat gagggttggg tcacgagtgt    180
ctgctgctgt tcaggcttat ccgggtggga caaagattaa caacaacctg taaatctgtt    240
ttttctcac aacgagtttt cttttttttg ccgaaaaagt cttttttgctg cttcactgtg     300
tagtgcggtg tgggtgtggc ggcaggtgtt gtgatctcca taactcccct cccatgcatc    360
atcatgacca gtgttgggta ctggtttgtt ggtgctgata ggggaacgtt atgtagagga    420
cccatagccg ttacacaacg tttccggcct cagtgtattg cagggacttt attctgtata    480
tactaacaga atgtatatat gaagccaaaa aaactttcag caatggatgt cttg          534
```

<210> SEQ ID NO 52
<211> LENGTH: 392
<212> TYPE: DNA
<213> ORGANISM: Eimeria gallopavonis

<400> SEQUENCE: 52

```
aagttgcgta aatagagccc tctaaaggat gcaaaagtcg taacacggtt tccgtaggtg      60
aacctgcgga aggatcattc acacgtataa agcatgaaag caggaagaga catatttctt    120
ttatttgatc tcctcctata tccttcttga gagatctgcg tttacgcggc ttgatcaagt    180
ttggtggtgg ttggtcaata gaagaggtgt cttttttgact ggtcttttca ggcttattat   240
gggataatat tcaaccgcaa cctgtaaatc tcttttttcct ctctcacaac aacgagtttt    300
ctgtagattg caattgatgc aagtgtattc tgtacgctac agaatataaa ggtacaaaaa    360
gaaaaaaaaa actttcagca atggatgtct tg                                  392
```

<210> SEQ ID NO 53
<211> LENGTH: 518
<212> TYPE: DNA
<213> ORGANISM: Eimeria gallopavonis

<400> SEQUENCE: 53

```
aagttgcgta aatagagccc tctaaaggat gcaaaagtcg taacacggtt tccgtaggtg      60
aacctgcgga aggatcattc acacgtaaag catgaaagca gggaaagata cttttttgatc    120
ttatccgttt gttgattgtt gtgggacagt cagcttgcat gcgggttggg tcacgagtgt    180
ctgctgctgt tcaggcttat ccgggtggga caaagattaa caacaacctg taaatctgtt    240
ttttctcac aacgagtttt cttttttttg ccgaaaaagt cttttttgctg cttcactgtg     300
tagtgcggtg tgggtgtggc ggcaggtgtt gtgatctcca taactcccct cccatgcatc    360
atcatgacca gtgttgggta ctggtttgtt ggtgctgata ggggaacgtt atgtagagga    420
cccatagccg ttacacaacg tttccggcct cagtgtattg cagggacttt attctgtata    480
tactaacaga atgtatatat gaagccaaaa aaactttc                             518
```

<210> SEQ ID NO 54
<211> LENGTH: 392
<212> TYPE: DNA
<213> ORGANISM: Eimeria gallopavonis

<400> SEQUENCE: 54

```
aagttgcgta aatagagccc tctaaaggat gcaaaagtcg taacacggtt tccgtaggtg      60
aacctgcgga aggatcattc acacgtataa agcatgaaag caggaagaga catatttctt    120
```

```
ttatttgatc tcctcctata tccttcttga gagatctgcg tttacgcggc ttgatcaagt      180
ttggtggtgg ttggtcaata gaagaggtgt cttttgact ggtcttttca ggcttattat       240
gggataatat tcaaccgcaa cctgtaaatc tcttttcct ctctcacaac aacgagtttt       300
ctgtagattg caattgatgc aagtgtattc tgtacgctac agaatataaa ggtgcaaaaa     360
gaaaaaaaaa actttcagca atggatgtct tg                                    392
```

```
<210> SEQ ID NO 55
<211> LENGTH: 532
<212> TYPE: DNA
<213> ORGANISM: Eimeria gallopavonis

<400> SEQUENCE: 55
aatgcgtaaa tagagccctc taaaggatgc aaaagtcgta acacggtttc cgtaggtgaa      60
cctgcggaag gatcattcac acgtaaagca tgaaagcagg gaaagatact ttttgatctt     120
atccgtttgt tgattgttgt gggacagtca gcttgcatgc gggttgggtc acgaatgtct     180
gctgctgttc aggcttatcc gggtgggaca agattaaca caacctgta aatctgtttt       240 tttctcacaa cgagttttct ttttttgcc gaaaagtct ttttgctgct tcactgtgta      300
gtgcggtgtg ggtgtggcgg caggtgttgt gatctccata actcccctcc catgcatcat     360
catgaccagt gttgggtact ggtttgttgg tgctgatagg ggaacgttat gtagaggacc     420
catagccgtt acacaacgtt tccggcctca gtgtattgca gggactttat tctgtatata     480
ctaacagaat gtatatatga agccaaaaaa actttcagca atggatgtct tg              532
```

```
<210> SEQ ID NO 56
<211> LENGTH: 417
<212> TYPE: DNA
<213> ORGANISM: Eimeria adenoeides

<400> SEQUENCE: 56
aagttgcgta aatagagccc tctaaaggat gcaaaagtcg taacacggtt tccgtaggtg      60
aacctgcgga aggatcattc acacgtgaag catgaaggca gagaaaggat gcttttgatc     120
agatatatct gctttgcttg taggtttgca ttggttcttg gtaacaagtc gccaagcaga     180
tttgcatgca tgcagttttg tgatcattat ttatagcgtc actttctttg actgctgttt     240
atgcttttgt tatggattgg acacacatta caaaatctgt aaatcttttt tcttttctca     300
caacgagttt tctctttgaa atttctggaa agaaagaata tagattgctg gctgtgtatg     360
taccagcaga atgtgtagaa tgaaaaagtt gaaaaacttt cagcaatgga tgtcttg        417
```

```
<210> SEQ ID NO 57
<211> LENGTH: 417
<212> TYPE: DNA
<213> ORGANISM: Eimeria adenoeides

<400> SEQUENCE: 57
aagttgcgta aatagagccc tctaaaggat gcaaaagtcg taacacggtt tccgtaggtg      60
aacctgcgga aggatcattc acacgtgaag catgaaggca gagaaaggat gcttttgatc     120
agatatatct gctttgcttg taggtttgca ttggttcttg gtaacaagtc gccaagcaga     180
tttgcatgca tgcagttttg tgatcattat ttatagcgtc actttctttg gctgctgttt     240
atgcttttgt tatggattgg acacacatta caaaatctgt aaatcttttt tcttttctca     300
caacgagttt tctctttgaa atttctggaa agaaagaata tagattgctg gctgtgtatg     360
taccagcaga atgtgtagaa tgaaaaagtt gaaaaacttt cagcaatgga tgtcttg        417
```

<210> SEQ ID NO 58
<211> LENGTH: 417
<212> TYPE: DNA
<213> ORGANISM: Eimeria adenoeides

<400> SEQUENCE: 58

```
aagttgcgta aatagagccc tctaaaggat gcaaaagtcg taacacggtt tccgtaggtg      60
aacctgcgga aggatcattc acacgtgaag catgaatgca gagaaaggat gcttttgatc     120
agatatatct gctttgcttg taggtttgca ttggttcttg gtaacaagtc gccaagcaga     180
tttgcatgca tgcagtttag tgatcattat ttatagcgtc tctttctttg actgctgttt     240
atgcttttgt tatggattgg acacacatta caaaatctgt aaatctttt tctttctca      300
caacgagttt tctctttgaa atttctggaa agaaagaata tagattgctg gctgtgtatg     360
taccagcaga atgtgtagaa tgaaaaagtt gaaaaacttt cagcaatgga tgtcttg       417
```

<210> SEQ ID NO 59
<211> LENGTH: 416
<212> TYPE: DNA
<213> ORGANISM: Eimeria adenoeides

<400> SEQUENCE: 59

```
aagttgcgta aatagagccc tctaaaggat gcaaaagtcg taacacggtt tccgtaggtg      60
aacctgcgga aggatcattc acacgtgaag catgaatgca gagaaaggat gcttttgatc     120
agatatatct gctttgcttg taggtttgca ttggttcttg gtaacaagtc gccaagcaga     180
tttgcatgca tgcagttttg tgatcattat ttatagcgtc tctttctttg actgctgttt     240
atgcttttgt tatgggttgg acacacatta caaaatctgt aaatctttt tctttctca      300
caacgagttt tctctttgaa atttctggaa agaaagaata tagattgctg gctgtgtatg     360
taccagcaga atgtgtagaa tgaaaaagtt gaaaaacttt cagcaatgga tgtctt        416
```

<210> SEQ ID NO 60
<211> LENGTH: 409
<212> TYPE: DNA
<213> ORGANISM: Eimeria dispersa

<400> SEQUENCE: 60

```
aagttgcgta aatagagccc tctaaaggat gcaaaagtcg taacacggtt tccgtaggtg      60
aacctgcgga aggatcattc acacattctg tccaacagga gctggtattc attcatttct    120
gtgtgaaatg gcatagatgg gtgttgcaag cttcctgtct tgggcggctg agtattgaac    180
cttttttatcc ctcccacaac ctttgaatcg gtttgttgag ttttcttcc acgacgagtt    240
ttcttaatat ttaaaagaat gaaagttgcg cccttgctgg ccactcattg agagccgcat    300
ttgtaactgc tctcgtgagc agtggaagcg gggcttttc agtgagtggc tgcatgcgcg    360
catgcgtaat atttatcagc tcttaaaact ttcagcaatg gatgtcttg               409
```

<210> SEQ ID NO 61
<211> LENGTH: 409
<212> TYPE: DNA
<213> ORGANISM: Eimeria dispersa

<400> SEQUENCE: 61

```
aagttgcgta aatagagccc tctaaaggat gcaaaagtcg taacacggtt tccgtaggtg      60
aacctgcgga aggatcattc acacattctg tccaacagga gctggtattc attcatttct    120
gtgtgaaatg gcacagatgg gtgttgcaag cttcctgtct tgggcggctg agtattgaac    180
```

```
cttttttatcc ctcccacaac ctttgaatcg gtttgttgag ttttctttcc acgacgagtt

```
<400> SEQUENCE: 65
aagttgcgta aatagagccc tctaaaggat gcaaaagtcg taacacggtt tccgtaggtg    60
aacctgcgga aggatcattc acacattttc ggtcgcgcga acaaaaggag cctctctctc   120
ctccgttcac tcctttctgc tgcaattcag tggaatgtgg ggtgtgcaga tggtcgtgtg   180
tgacggcttt ttgtcttgtt ggccgactgg aatcctttt gaaccttttt aattcctccc    240
aacctttgaa tcggttaaga gttttcttcc cacgacgagt tttctttgag aataaaagag   300
aatgtgttgc gcaggtggct gctcgctcgt tgagagtggc tgggctgcat acgcgcatgc   360
gaagcgagaa aaaggaccc aaaactttca gcaatggatg tcttg                    405

<210> SEQ ID NO 66
<211> LENGTH: 407
<212> TYPE: DNA
<213> ORGANISM: Eimeria meleagrimitis 1

<400> SEQUENCE: 66
aagttgcgta aatagagccc tctaaaggat gcaaaagtcg taacacggtt tccgtaggtg    60
aacctgcgga aggatcattc acacattttc ggtcgcgcga acaaaaggag cctctctctc   120
ctccgttcac tcctttctgc tgcaattcag tggaatgtgg ggtgtgcaga tggtcgtgtg   180
tgacggcttt ttgtcttgtt ggccgactgg aatcctttt gaaccttttt aattcctccc    240
aacctttgaa tcggttaaga gttttcttcc cacgacgagt tttctttgag aataaaagag   300
atgtgttgcg caggtggctg ctcgctcgtt gagagtggct gggctgcatg ctgcgcgcat   360
gcgaagagag aaaaaaggac ccaaaacttt cagcaatgga tgtcttg                 407

<210> SEQ ID NO 67
<211> LENGTH: 405
<212> TYPE: DNA
<213> ORGANISM: Eimeria meleagrimitis 1

<400> SEQUENCE: 67
aagttgcgta aatagagccc tctaaaggat gcaaaagtcg taacacggtt tccgtaggtg    60
aacctgcgga aggatcattc acacattttc ggtcgcgcga acaaaaggag cctctctctc   120
ctccgttcac tcctttctgc tgcaattcag tggaatgtgg ggtgtgcaga tggtcgtgtg   180
tgacggcttt ttgtcttgtt ggccgactgg aatcctttt gaaccttttt aattcctccc    240
aacctttgaa tcggttaaga gttttcttcc cacgacgagt tttctttgag aataaaagag   300
aatgtgttgc gcaggtggct gctcgctcgt tgagagtggc tgggctgcat gcgcgcatgc   360
gaagagagaa aaaggaccc aaaactttca gcaatggatg tcttg                    405

<210> SEQ ID NO 68
<211> LENGTH: 405
<212> TYPE: DNA
<213> ORGANISM: Eimeria meleagrimitis 1

<400> SEQUENCE: 68
aagttgcgta aatagagccc tctaaaggat gcaaaagtcg taacacggtt tccgtaggtg    60
aacctgcgga aggatcattc acacattttc ggtcgcgcga acaaaaggag cctctctctc   120
ctccgttcac tcctttctgc tgcaattcag tggaatgtgg ggtgtgcaga tggtcgtgtg   180
tgacggcttt ttgtcttgtt ggccgactgg aatcgttttt gaaccttttt aattcctccc    240
aacctttgaa tcggttaaga gttttcttcc cacgacgagt tttctttgag aataaaagag   300
aatgtgttgc gcaggtggct gctcgctcgt tgagagtggc tgggctgcat gcgcgcatgc   360
```

|  |  |
|---|---|
| gaagagagaa aaaaggaccc aaaactttca gcaatggatg tcttg | 405 |

<210> SEQ ID NO 69
<211> LENGTH: 500
<212> TYPE: DNA
<213> ORGANISM: Eimeria meleagrimitis 2

<400> SEQUENCE: 69

|  |  |
|---|---|
| aagttgcgta aatagagccc tctaaaggat gcaaaagtcg taacacggtt tccgtaggtg | 60 |
| aacctgcgga aggatcattc acacgtgatg catgcagcaa gctggaaagg tgcctgtttg | 120 |
| tatgtgggaa gtgcatttat tatgcacacc tgcattcatg cgaggttact gtcaatccgg | 180 |
| cgactgcatg tatggcttct tggaccgcaa taacaacctg taaatctctt ttcttctcca | 240 |
| caacggtttt tcttttgttt acggtacttt atttgtgtac cacaactata agttgttggg | 300 |
| gttttcagct gcttcactgt gctactggat gataggctag ctgcatttgt tttgccggtc | 360 |
| ggggttgttg ttcggcaggc acagcatggc agcagggctg tcggcagtgg caggtgtttg | 420 |
| cagttgtgta ccatttaatt ctgctaaaga gcagaatgat ttgtttacaa aaaaaaaaac | 480 |
| tttcagcaat ggatgtcttg | 500 |

<210> SEQ ID NO 70
<211> LENGTH: 502
<212> TYPE: DNA
<213> ORGANISM: Eimeria meleagrimitis 2

<400> SEQUENCE: 70

|  |  |
|---|---|
| aagttgcgta aatagagccc tctaaaggat gcaaaagtcg taacacggtt tccgtaggtg | 60 |
| aacctgcgga aggatcattc acacgtgatg catgcagcaa gctggaaagg tgcctgtttg | 120 |
| tatgtgggaa gtgcatttct tatgcacacc tgcatgcatg tgaggttact gtcaagccgg | 180 |
| cgactgcatg tatggcttct tggaccgcaa taacaacaac ctgtaaatct cttttcctct | 240 |
| ccacaacggt ttttcttttg tttacggtac tttatttgtg taccacaact ataagttctt | 300 |
| ggggttttca gctgcttcac tgtgctactg gatgataggc tagctgcatt tgttttgcca | 360 |
| gtcggggttg ctgtttggca ggcacagcat ggcagcaggg gtgttggcag ttgcagtgtt | 420 |
| tgcagttgta taccatttaa ttctgctgaa gagcagaatg ttttgtttac aaaaaaaaaa | 480 |
| actttcagca atggatgtct tg | 502 |

<210> SEQ ID NO 71
<211> LENGTH: 503
<212> TYPE: DNA
<213> ORGANISM: Eimeria meleagrimitis 2

<400> SEQUENCE: 71

|  |  |
|---|---|
| aagttgcgta aatagagccc tctaaaggat gcaaaagtcg taacacggtt tccgtaggtg | 60 |
| aacctgcgga aggatcattc acacgtgatg catgcagcaa gctggaaagg tgcctgtttg | 120 |
| tatgtgggaa gtgcatttct tatgcacacc tgcatgcatg tgaggttact gtcaagccgg | 180 |
| cgactgcatg tatggcttct tggaccgcaa taacaacaac ctgtaaatct cttttcctct | 240 |
| ccacaacggt ttttcttttg tttacggtac tttatttgtg taccacaact ataagttctt | 300 |
| ggggttttca gctgcttcac tgtgctactg gatgataggc tagctgcatt tgttttgcca | 360 |
| gtcggggttg ctgtttggca ggcacagcat ggcagcaggg gtgttggcag ttgcagtgtt | 420 |
| tgcagttgta taccatttaa ttctgctgaa gagcagaatg ttttgtttac aaaaaaaaaa | 480 |
| aactttcagc aatggatgtc ttg | 503 |

<210> SEQ ID NO 72
<211> LENGTH: 501
<212> TYPE: DNA
<213> ORGANISM: Eimeria meleagrimitis 2

<400> SEQUENCE: 72

```
aagttgcgta aatagagccc tctaaaggat gcaaaagtcg taacacggtt ccgtaggtg       60
aacctgcgga aggatcattc acacgtgatg catgcagcaa gctggaaagg tgcctgtttg      120
tatgtgggaa gtgcatttct tatgcacacc tgcatgcatg tggggttact gtcaatccgg      180
cgactgcatg tatggcttct tggaccgcaa taacaacaac ctgtaaatct cttttcttct      240
ccacaacggt ttttcctttg tttacggtgc tttatttgtg taccacaact ataagttgtt      300
ggggttttca gctgcttcac tgtgctactg gatgaccggc tagctgcatt tattttgcca      360
gtcggggttg ctgttcggca ggcacagcat ggcagcaggg ctgtcggcag tggcaggtgt      420
ttgcagttgt ataccattta attctgctga agagcagaat gttttgttta caaaaaaaaa      480
ctttcagcaa tggatgtctt g                                               501
```

<210> SEQ ID NO 73
<211> LENGTH: 475
<212> TYPE: DNA
<213> ORGANISM: Eimeria meleagrimitis 2

<400> SEQUENCE: 73

```
gcatgcagtc gtacacggtt ccgtaggtg aacctgcgga aggatcattc acacgtgatg       60
catgcagcaa gctggaaagg tgcctgtttg tatgtgggaa gtgcatttct tatgcacacc      120
tgcattcatg cgaggttact gtcaatccgg cgactgcatg tatggcttct tggaccgcaa      180
taacaacaac ctgtaaatct cttttcctct ccacaacggt ttttcttttg tttacggtac      240
tttatttgtg taccacaact ataagttgtt ggggttttca gctgcttcac tgtgctactg      300
gatgataggc tagctgcatt tgttttgccg gtcggggttg ttgttcggca ggcacagcat      360
ggcagcaggg ctgtcggcag tggcaggtgt ttgcagttgt ataccattta attctgctaa      420
aaagcaaaat gttttgttta caaaaaaaaa atttttcaac ggtggttttg aggaa          475
```

<210> SEQ ID NO 74
<211> LENGTH: 506
<212> TYPE: DNA
<213> ORGANISM: Eimeria gallopavonis

<400> SEQUENCE: 74

```
gtcgtcaagt cgtacacggt ttccgtaggt gaacctgcgg aaggatcatt cacacgtaaa       60
gcatgaaagc agggaaagat acttttttgat cttatccgtt tgttgattgt tgtgggacag     120
tcagcttgca tgcgggttgg gtcacgagtg tctgctgctg ttcaggctta tccgggtggg      180
acaaagatta acaacaacct gtaaatctgt tttttttctca caacgagttt tcttttttttt     240
gccgaaaaag tctttttgct gcttcactgt gtagtgcggt gtgggtgtgg cggcaggtgt      300
tgtgatctcc ataactcccc tcccatgcat catcatgacc agtgttgggt actggtttgt      360
tggtgctgat aggggaacgt tatgtagagg acccatagcc gttacacaac gtttccggcc      420
tcagtgtatt gcagggactt tattctgtat atactaacag aatgtatata tgaagccaaa      480
aaaactttca gcaatggatg tcttga                                          506
```

<210> SEQ ID NO 75
<211> LENGTH: 417
<212> TYPE: DNA

<213> ORGANISM: Eimeria adenoeides

<400> SEQUENCE: 75

| aagttgcgta aatagagccc tctaaaggat gcaaaagtcg taacacggtt tccgtaggtg | 60 |
| aacctgcgga aggatcattc acacgtgaag catgaakgca gagaaggat gcttttgatc | 120 |
| agatatatct gctttgcttg taggtttgca ttggttcttg gtaacaagtc gccaagcaga | 180 |
| tttgcatgca tgcagttttg tgatcattat ttatagcgtc tctttctttg actgctgttt | 240 |
| atgcttttgt tatggattgg acacacatta caaaatctgt aaatctttt tcttttctca | 300 |
| caacgagttt tctcttttgaa atttctggaa agaaagaata tagattgctg gctgtgtatg | 360 |
| taccagcaga atgtgtagaa tgaaaaagtt gaaaaacttt cagcaatgga tgtcttg | 417 |

<210> SEQ ID NO 76
<211> LENGTH: 403
<212> TYPE: DNA
<213> ORGANISM: Eimeria meleagrimitis 1

<400> SEQUENCE: 76

| aagttgcgta aatagagccc tctaaaggat gcaaaagtcg taacacggtt tccgtaggtg | 60 |
| aacctgcgga aggatcattc acacattttc ggtcgcgcga acaaaaggag cctctctctc | 120 |
| ctccgttcac tcctttctgc tgcaattcag tggaatgtgg ggtgtgcaga tggtcgtgtg | 180 |
| tgacggcttt ttgtcttgtt ggccgactgg aatcctttt gaaccttttt aattcctccc | 240 |
| aaccttttgaa tcggttaaga gttttcttcc cacgacgagt tttctttgag aataaaagag | 300 |
| aatgtgttgc gcaggtggct gctcgctcgt tgagagtggc tgggctgcat gcgcgcatgc | 360 |
| gaagagagaa aaaaggaccc aaaactttca gcaatggatg tct | 403 |

<210> SEQ ID NO 77
<211> LENGTH: 538
<212> TYPE: DNA
<213> ORGANISM: Eimeria gallopavonis

<400> SEQUENCE: 77

| taagttgcgg taaatagagc cctctaaagg atgcaaaagt cgtaacacgg tttccgtagg | 60 |
| tgaacctgcg gaaggatcat tcacacgtaa agcatgaaag cagggaaaga tacttttga | 120 |
| tcttatccgt ttgttgattg ttgtgggaca gtcagcttgc atgcgggttg ggtcacgagt | 180 |
| gtctgctgct gttcaggctt atccgggtgg gacaaagatt aacaacaacc tgtaaatctg | 240 |
| ttttttctc acaacgagtt ttcttttttt tgccgaaaaa gtcttttgc tgcttcactg | 300 |
| tgtagtgcgg tgtgggtgtg gcggcaggtg ttgtgatctc cataactccc ctcccatgca | 360 |
| tcatcatgac cagtgttggg tactggtttg ttggtgctga taggggaacg ttatgtagag | 420 |
| gacccatagc cgttacacaa cgtttccggc ctcagtgtat tgcagggact ttattctgta | 480 |
| tatactaaca gaatgtatat atgaagccaa aaaaactttc agcaatggaa tgtcttga | 538 |

<210> SEQ ID NO 78
<211> LENGTH: 392
<212> TYPE: DNA
<213> ORGANISM: Eimeria gallopavonis

<400> SEQUENCE: 78

| aagttgcgta aatagagccc tctaaaggat gcaaaagtcg taacacggtt tccgtaggtg | 60 |
| aacctgcgga aggatcattc acacgtataa agcatgaaag caggaagaga catatttctt | 120 |
| ttatttgatc tcctcctata tccttcttga gagatctgcg tttacgcggc ttgatcaagt | 180 |

```
ttggtggtgg ttggtcaata gaagaggtgt cttttttgact ggtcttttca ggcttattat    240
gggataatat tcaaccacaa cctgtaaatc tcttttttcct ctctcacaac aacgagtttt    300
ctgtagattg caattgatgc aagtgtattc tgtacgctac agaatataaa ggtacaaaaa    360
gaaaaaaaaa aactttcagc aatggatgtc tt                                   392

<210> SEQ ID NO 79
<211> LENGTH: 355
<212> TYPE: DNA
<213> ORGANISM: Eimeria gallopavonis

<400> SEQUENCE: 79
gtaatcagtc gtacacggtt tccgtaggtg aacctgcgga aggatcattc acacgtataa     60
agcatgaaag caggaagaga catatttctt ttatttgatc tcctcctata tccttcttga    120
gagatctgcg tttacgcggc ttgatcaagt ttggtggtgg ttggtcaata gaagaggtgt    180 cttttttgact ggtcttttca ggcttattat gggataatat tcaaccgcaa cctgtaaatc    240 tcttttttcct ctctcacaac aacgagtttt ctgtagattg caattgatgc aagtgtattc    300
tgtacgctac agaatataaa ggtacaaaaa gaaaaaaaaa actttcagca aggga         355

<210> SEQ ID NO 80
<211> LENGTH: 373
<212> TYPE: DNA
<213> ORGANISM: Eimeria dispersa

<400> SEQUENCE: 80
tagatcagtc gtacacggtt tccgtaggtg aacctgcgga aggatcattc acacattctg     60
tccaacagga gctggtattc attcatttct gtgtgaaatg gcacagatgg gtgttgcaag    120
cttcctgtct tgggcggctg ggtattgaac ctttttatcc ctcccacaac ctttgaatcg    180
gtttgttgag ttttctttcc acgacgagtt ttcttaaaat ttaaaagaat gaaagttgcg    240
cccttgctgg tcactcattg agagccgcat ttgtaactgc tctcgagagc agtggaagcg    300 gggctttttta agtgagtggc tgcatgcgcg catgcgtaat atttatcagc tcttaaaact    360
ttcagcatgg aaa                                                        373

<210> SEQ ID NO 81
<211> LENGTH: 268
<212> TYPE: DNA
<213> ORGANISM: Eimeria meleagrimitis 2

<400> SEQUENCE: 81
cggtttccgt aggtgaacct gcggaaggat cattcacacg tgatgcatgc agcaagctgg     60
aaaggtgcct gtttgtatgt gggaagtgca tttcttatgc acacctgcat gcatgtgagg    120
ttactgtcaa tccggcgact gcatgtatgg cttcttggac cgcaataaca acaacctgta    180
aatctctttt cctctccaca acggttttttc ttttgtttac ggtactttat ttgtgtacca    240
caactataag ttgttggggt tttcagct                                        268
```

We claim:

1. A vaccine composition comprising isolated *E. meleagrimitis* 2 and *E. meleagrimitis* 1.

2. The vaccine of claim 1 further comprising one or more additional *Eimeria* species selected from the group consisting of *E. adenoeides, E. gallopavonis, E. dispersa, E. innocua*, and *E. subrotunda*.

3. The vaccine of claim 2 wherein the additional *Eimeria* species is *E. adenoeides*.

4. The vaccine of claim 3 further comprising *E. meleagridis*.

5. The vaccine of claim 3 further comprising *E. dispersa*.

6. The Vaccine of claim 1 further comprising a parasite from the coccidia genus selected from the group consisting of *Isospora, Cystoisospora*, and *Cryptosporidium*.

7. The vaccine of claim 1 wherein the *E. meleagrimitis* 2 is an unattenuated strain.

8. The vaccine of claim 7 wherein the *E. meleagrimitis* 1 is an unattenuated strain.

9. The vaccine of claim 8 that comprises from about 10 to about 1000 oocysts of each of *E. meleagrimitis* 2 and *E. meleagrimitis* 1.

10. The vaccine of claim 1 wherein the *E. meleagrimitis* 2 is an attenuated strain.

11. The vaccine of claim 10 wherein the *E. meleagrimitis* 1 is an attenuated strain.

12. The vaccine of claim 11 in which the quantity of oocysts is from about 100 to about 10,000 oocysts of each of *E. meleagrimitis* 2 and *E. meleagrimitis* 1.

13. The vaccine of claim 1 that comprises merozoites.

14. A method of immunizing a turkey against *E. meleagrimitis* 2 and *E. meleagrimitis* 1 comprising administering to the animal an immunologically effective amount of the vaccine of claim 1.

15. The method of claim 14 wherein the vaccine is administered in the drinking water of the turkey.

16. The method of claim 14 wherein the vaccine is administered in the food of the turkey.

17. A method of immunizing a turkey against *E. meleagrimitis* 2 comprising administering to the turkey a vaccine comprising an immunologically effective amount of isolated *E. meleagrimitis* 2.

18. The method of claim 17 further comprising administering to the turkey one or more additional vaccines against a species of *Eimeria* other than *E. meleagrimitis* 2, wherein each additional vaccine comprises an immunologically effective amount of one or more *Eimeria* species selected from the group consisting of *E. adenoeides, E. gallopavonis, E. dispersa, E. meleagridis, E. innocua,* and *E. subrotunda;* wherein the administration of the vaccine against *E. meleagrimitis* 2 and the administration of one or more additional vaccines against a species of *Eimeria* other than *E. meleagrimitis* 2 can be performed in any order, including simultaneously in a combined administration.

* * * * *